(12) United States Patent
Antoncic et al.

(10) Patent No.: US 7,271,269 B2
(45) Date of Patent: Sep. 18, 2007

(54) PREPARATION OF NEW PHARMACEUTICALLY SUITABLE SALT OF LOSARTAN AND FORMS THEREOF WITH NEW PURIFICATION AND ISOLATION METHODS

(75) Inventors: Ljubomir Antoncic, Ljubljana (SI); Anton Copar, Smartno pri Litiji (SI); Peter Svete, Borovnica (SI); Breda Husu-Kovacevic, Ljubljana (SI); Zoran Ham, Trbovlje (SI); Boris Marolt, Trzin (SI)

(73) Assignee: Lek Pharmaceuticals D.D., Lujbijene (SI)

( * ) Notice: Subject to any disclaimer, the term of this patent is extended or adjusted under 35 U.S.C. 154(b) by 10 days.

(21) Appl. No.: 10/524,993

(22) PCT Filed: Jan. 29, 2004

(86) PCT No.: PCT/SI2004/000001

§ 371 (c)(1),
(2), (4) Date: Feb. 18, 2005

(87) PCT Pub. No.: WO2004/066997

PCT Pub. Date: Aug. 12, 2004

(65) Prior Publication Data

US 2006/0004207 A1    Jan. 5, 2006

(30) Foreign Application Priority Data

Jan. 30, 2003 (SI) ............................... 200300025
Jan. 30, 2003 (SI) ............................... 200300026
Jun. 12, 2003 (SI) ............................... 200300145
Jun. 26, 2003 (SI) ............................... 200300157
Nov. 5, 2003 (SI) ............................... 200300270

(51) Int. Cl.
*C07D 257/04* (2006.01)
(52) U.S. Cl. ...................................... 548/252
(58) Field of Classification Search ................. 548/252
See application file for complete search history.

(56) References Cited

U.S. PATENT DOCUMENTS 5,795,904 A    8/1998    Cohen
5,962,500 A    10/1999   Eide et al.
2004/0097568 A1*  5/2004    Reddy et al. ............... 514/381

OTHER PUBLICATIONS

Brittain in Polymorphism in Pharmacetical Solids (1999).*
Elbary et al., "Polymorphic Transformation of Losartan", Egypt. J. Pharm. Sci., vol. 40, No. 1, pp. 49-59 (1999).

* cited by examiner

*Primary Examiner*—Joseph K. McKane
*Assistant Examiner*—Andrew B. Freistein
(74) *Attorney, Agent, or Firm*—John D. Thallemer

(57) ABSTRACT

Pharmaceutically suitable crystalline and amorphous alkali and earth-alkali salts of 2-n-butyl-4-chloro-5-hidrox-ymethyl-1-[[2'-(1 H-tetrazole-5-yl)[1.1'-biphenyl]-4-yl]-1 Himidazole have been prepared and new manufacturing, purification and isolation procedure for said salts in high purity have been described. Stable pharmaceutical compositions containing new crystalline potassium salts of 2-n-butyl-5-chloro-5hidroxymethyl-1-[[2'-(1H-tetrazole-5-yl)[1.1'-biphenyl]-44-yl]-1H-imidazole have been prepared.

5 Claims, 32 Drawing Sheets

PREPARATION OF NEW PHARMACEUTICALLY SUITABLE SALT OF LOSARTAN AND FORMS THEREOF WITH NEW PURIFICATION AND ISOLATION METHODS

FIELD OF THE INVENTION (IPC$^7$ A 61 K, A 61 K 9/19)

The disclosed invention lies within the field of heterocyclic chemistry and pharmaceutical industry, and relates to a new method for preparing pharmaceutically suitable crystalline and amorphous alkali and earth-alkali salts of 2-n-butyl-4-chloro-5-hidroxymethyl-1-[[2'-(1H-tetrazole-5-yl)[1,1'-biphenyl]-4-yl]-1H-imidazole known by the generic name losartan and new purification and isolation procedure for said salts with aim of obtaining same in high purity for incorporation thereof into pharmaceutical compositions.

TECHNICAL PROBLEM 2-n-butyl-4-chloro-5-hidroxymethyl-1-[[2'-(1H-tetrazole-5-yl)[1,1'-biphenyl]-4-yl]-1H-imidazole has a pharmacological effect on the last step of renin-angiotensin cascade system by binding to angiotensin II receptor. By virtue of this biochemical effect losartan is generally used as an effective anti-hypertensive in form of its potassium salt (from hereon losartan potassium).

STATE OF THE ART

Substituted imidazoles with effect of rennin-angiotensin system of blood pressure regulation, which include losartan, were disclosed in patents EP 253310 and U.S. Pat. No. 5,138,069.

By the patentees of EP 253310 protection was claimed for various substituted imidazoles and salts thereof among them to be named ammonium, calcium, potassium, and sodium salts. Specifically reactions were described which yielded potassium and sodium salts of certain substituted imidazoles, and products thereof were characterized. Surprisingly, a 2-n-butyl-4-chloro-5-hidroxymethyl-1-[[2'-(1H-tetrazole-5-yl)[1,1'-biphenyl]-4-yl]-1H-imidazole,) later named losartan, was described only in its amphoteric form, In the experimental section of this patent it is mentioned that at the synthesis of losartan from cyano biphenyl intermediate (i.e., from 2-n-butyl-4-chloro-5-hidroxymethyl-1-[[2'-cyanobiphenyl]-4-yl]-1H-imidazole) with sodium azide losartan precipitates in the from of pale yellow crystals. According to the patent, also the blood pressure lowering effect was on animals compared, of furosemide with sodium salt of 2-n-butyl-4-chloro-5-hidroxymethyl-1-[[2'-(1H-tetrazole-5-yl)[1,1'-biphenyl]-4-yl]-1H-imidazole, but said salt is not characterized nor is it included in the Chemical Abstracts registry.

In the Chemical Abstracts registry there are among the compounds with losartan structural formula or salts thereof mentioned losartan in its amphoteric form. compounds with tetrahydrofuran and pyridin, a mixture with hydrochlorotiazide, acid addition complexes hydrobromide, and hydrochloride, among the salts p-toluene sulphonate and potassium salt as well as hydrochloride of potassium salt, which indicates that other alkali or earth-alkali salts were not characterized nor are their useful properties known.

In order to facilitate incorporation into a pharmaceutical composition, an active pharmaceutical ingredient should posses certain desired physical and chemical properties, i.e., solubility in water and certain solvents, adequate particle size, stability, hydroscopic properties, which can be regulated by the choice of suitable salt, complex and form, which allows reaching an effective bio-availability.

Alkali and earth-alkali salts of losartan can be prepared due to acidic hydrogen atom on tetrazole ring, which can be deprotonated by using a base of sufficient strength, i.e., one with which an equivalent point of water solution can be reached. According to patent U.S. Pat. No. 5,310,928 this is around a pH=10, EP 324377 describes a process for forming losartan potassium with potassium hydroxide, whereupon potassium salt was adopted as the most convenient for galenic use.

A similar process of preparing crystalline losartan potassium is described in patent application WO 02094816, according to which solid potassium hydroxide is added to an alcohol solution of losartan instead of using potassium hydroxide dissolved in water.

According to the synthesis process described in patents U.S. Pat. No. 5,130,439 and U.S. Pat. No. 5,310,928, proceeding over substituted boron salts, hydrolysis of 2-n-butyl-4-chloro-5-hidroxymethyl-1-[[2'-(2-triphenylmethyl-2H-tetrazole-5-yl)[1,1'-biphenyl]-4-yl]-1H-imidazole with sulphuric acid in THF with subsequent elution on a column with dipotassium hydrogenphosphate, and concentration of eluted aqueous solution while adding iso-propanol, yields a crystalline losartan potassium. In the patent also preparation by spray drying is mentioned.

Therefore, usually losartan is converted into losartan potassium by a base, which is a potassium hydroxide or dipotassium hydrogenphosphate. In general, it is also possible to prepare salts of certain heterocyclic compounds in nonaqueous conditions by using alcoholates of alkali or earth alkali metals, which has been achieved according to the teaching of EP 495626 on some tetrazole, but not on losartan.

It is known that losartan potassium exists in at least two polymorph forms [Pharm. Res. 10 (1993), 900]. The authors of U.S. Pat. No. 5,608,075 teach that polymorph Form I, characterized by DSC endotherm at 229.5° C., converts, while heated, into polymorph Form II, characterized by endotherm melting point at 273.2° C. Crystalline forms of losartan potassium were extensively studied, and in all the prepared forms it appeared as a crystalline product. Crystalline forms prepared using surfactants were characterized and described in Egypt. J. Pharm. Sci., 40, (1999), 49.

From the description of U.S. Pat. No. 5,859,258, which teaches crystallization of losartan potassium Form I from a mixture of isopropanol and 2.4-2.6% water, it is evident that the defined polymorph only does not necessarily provide suitable physical and chemical properties. It was discovered that uncontrolled crystallization could yield large tridemsional aggregates, which are not suitable for incorporation into pharmaceutical composition. With respect to the present invention, the patent teaches a strictly controlled process in which, surprisingly, not less than fourteen process parameters must be met to yield suitable particles for galenic use. A need for such strictly controlled process can in conditions of industrial production lead to higher number of mistakes, which can influence the end product.

The authors of the patent U.S. Pat. No. 5,128,355 have prepared and synthesized certain compounds, which are structurally very similar to losartan. Bromo and iodo analogs of losartan potassium are amorphous substances. Amorphous is also a compound, 2-n-propyl-4-chloro-5-hidroxymethyl-1-[[2'-(1H-tetrazole-5-yl)[1,1'-biphenyl]-4-yl]-1H- imidazole, which differs from losartan only by a single carbon atom on the side chain.

Until the priority date of the present application there has been published no method for preparing amorphous forms of salts of losartan. It is known that in certain cases, when pure pharmaceutical active substances cannot be obtained in an amorphous form, certain excipients are added, which cause the formation of a solid without formation of a repeating crystal lattice, which is a characteristic of an amorphous state. WO 0142221 teaches formation of amorphous celecoxib with addition of crystallization inhibitors, such as polyvinyl pyrolidone or hydroxypropyl methylcellulose. Obtained composites exhibited increased bio-availability due to their amorphous nature. The addition of surfactants to losartan potassium according to the Egypt. J. Pharm. Sci., 40, (1999), 49 afforded only crystalline structures. U.S. Pat. No. 6,284,277 describes a pharmaceutical composition obtained by lyophilisation, according to which the amorphous phase and the crystalline phase are combined, specifically substantially amorphous active ingredients and manitol were combined with substantially crystalline alanine.

The authors of WO 03048135, which was published after the priority date of present application, have prepared amorphous losartan potassium and a crystalline structure with bound between 12% and 16% of water, which they named Form III, and two further crystalline polymorph forms: one with strongest diffractions in powder X-ray difractogram at around 2θ=4.3, 15.6, and 23.4°, which they named Form IV and other with strongest diffractions in powder X-ray difractogram at around 2θ=6.4, 12.2, 20.7, 21.5 and 22.5°, which they named Form V. WO 03048135 teaches preparation of Form IV by dissolving losartan potassium in a solvent with a boiling point below 135° C., and addition of dichloromethane, whereupon a suspension is formed, and a preparation of Form V by dissolving losartan potassium in a solvent with a boiling point below 135° C., and addition of hexane. According to WO 03048135, as most suitable solvents, $C_1$ to $C_6$ alcohols have been found, however, in all of the examples only ethanol is mentioned.

It is known that due to intake into the body, special levels of purity of pharmaceutically active ingredients are required in order to avoid unwanted and toxic effects. Substances are purified by different methods, for solids, e.g., thermal and other crystallizations, precipitations with solvents or reagents, extractions and rinsings, pH regulations, chromatographic methods are applied. By the authors of EP 253310, the end product was purified by crystallization of amphoter from acetonitrile. In later publications, e.g., WO 9310106 and WO 9517396, more complex and longer procedures to assure high purity of losartan potassium are described, which comprise thermal crystallizations of amphopter and potassium salt, use of column chromatography, and use of adsorbtion resins. Authors of EP 1106611 and U.S. Pat. No. 6,350,880 claim said methods to be unsatisfactory, and propose purification through acid salts of losartan as chlorides, bromides and p-toluensulphonates. The end phase is nevertheless a single step crystallization from acid salt into alkali salt with KOH, in which larger quantities of potassium salt of the anion part of the losartan are formed, which can coprecipitate to losartan potassium as an impurity. The end step is performed in acetonitrile, which due to its toxicity is not a preferred solvent.

EP 324377 describes pharmaceutical compositions, in which from 1 to 500 mg losartan daily are combined with other substances, e.g., diuretics, and teaches the use for treatment of hypertension. WO 9119228 describes optimised compositions of tablets suitable for direct compression.

DETAILED DESCRIPTION OF THE INVENTION

Figure 1:
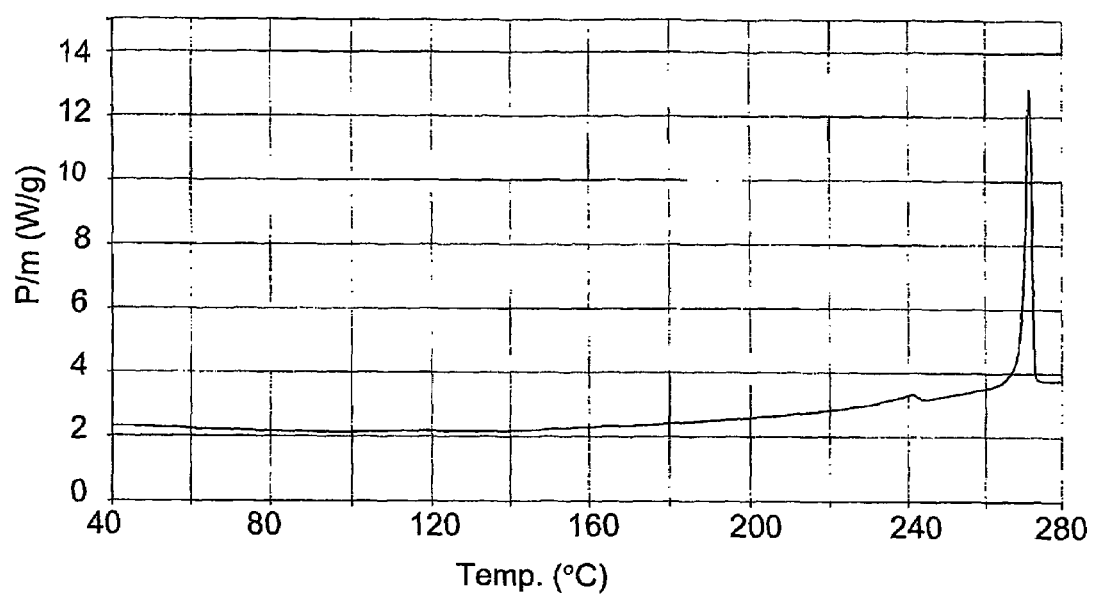
FIG. 1: DSC thermogram of crystalline potassium salt of losartan (Form I)
Figure 2:
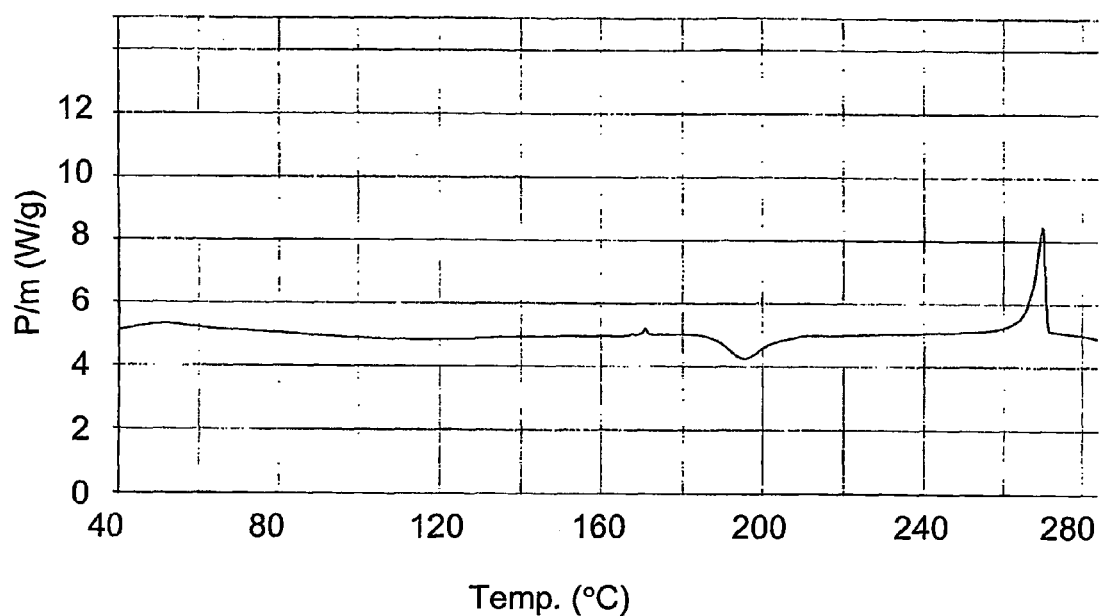
FIG. 2: DSC thermogram of amorphous potassium salt of losartan
Figure 3:
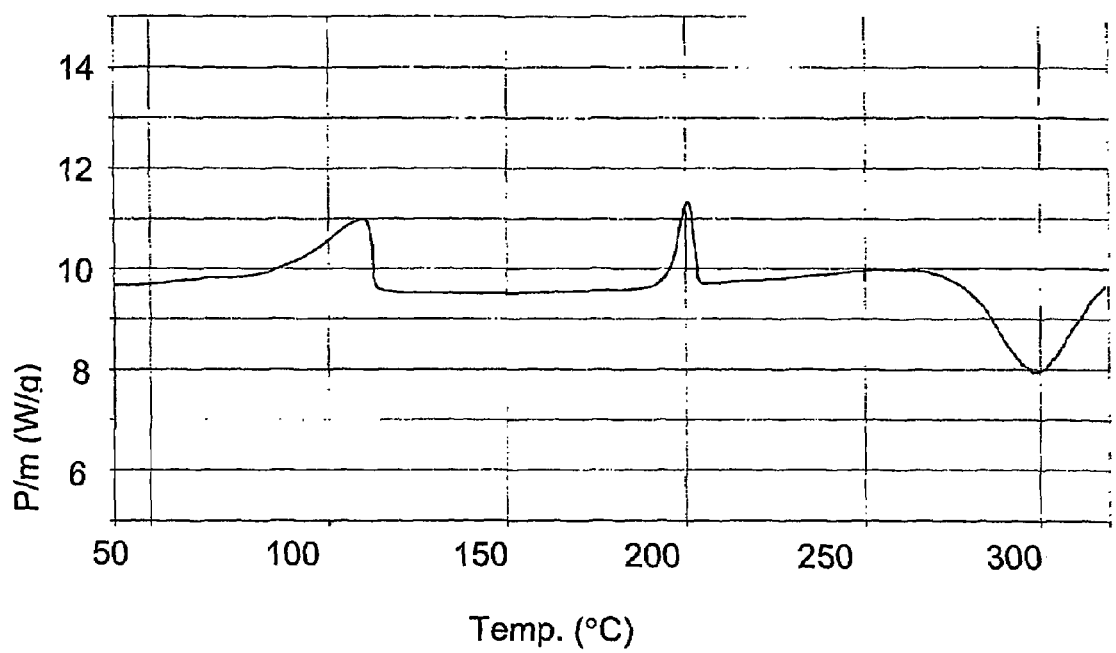
FIG. 3: DSC thermogram of crystalline sodium salt of losartan
Figure 4:
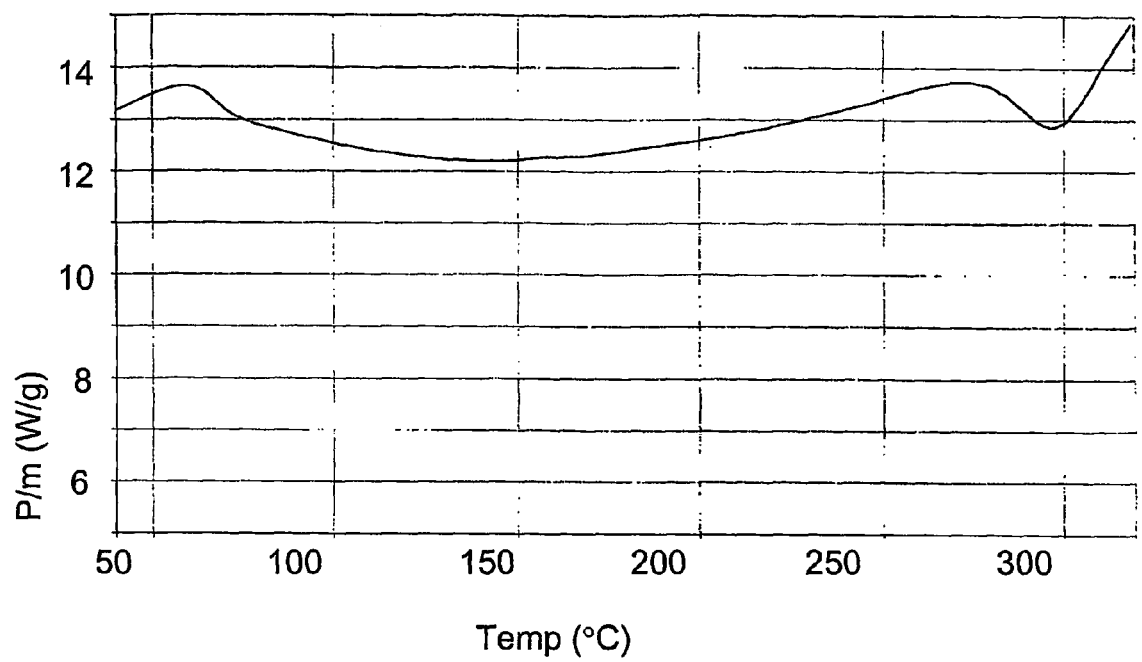
FIG. 4: DSC thermogram of amorphous sodium salt of losartan
Figure 5:
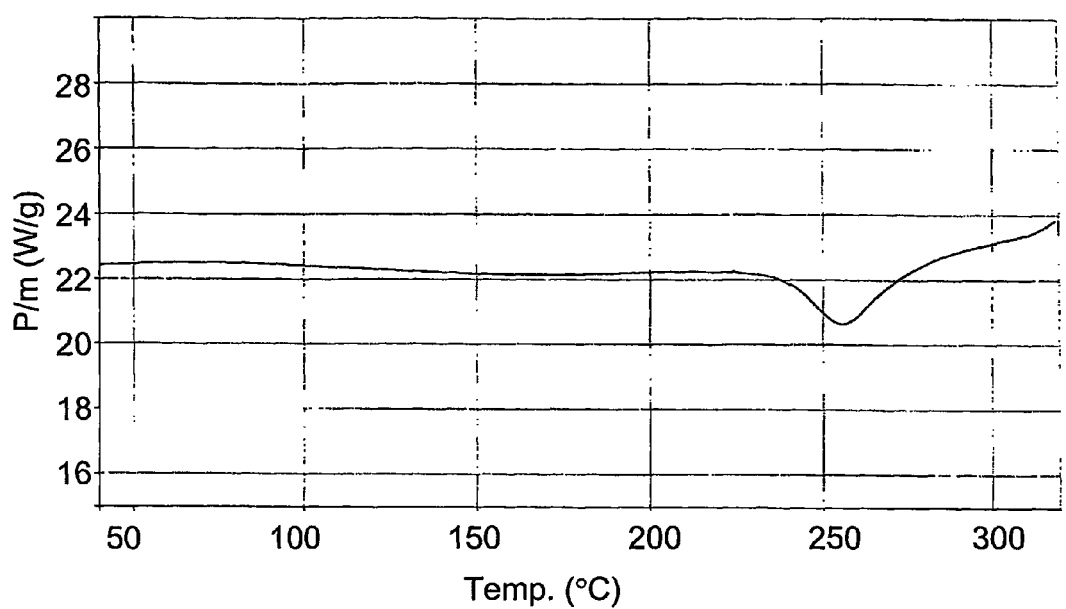
FIG. 5: DSC thermogram of magnesium salt of losartan
Figure 6:
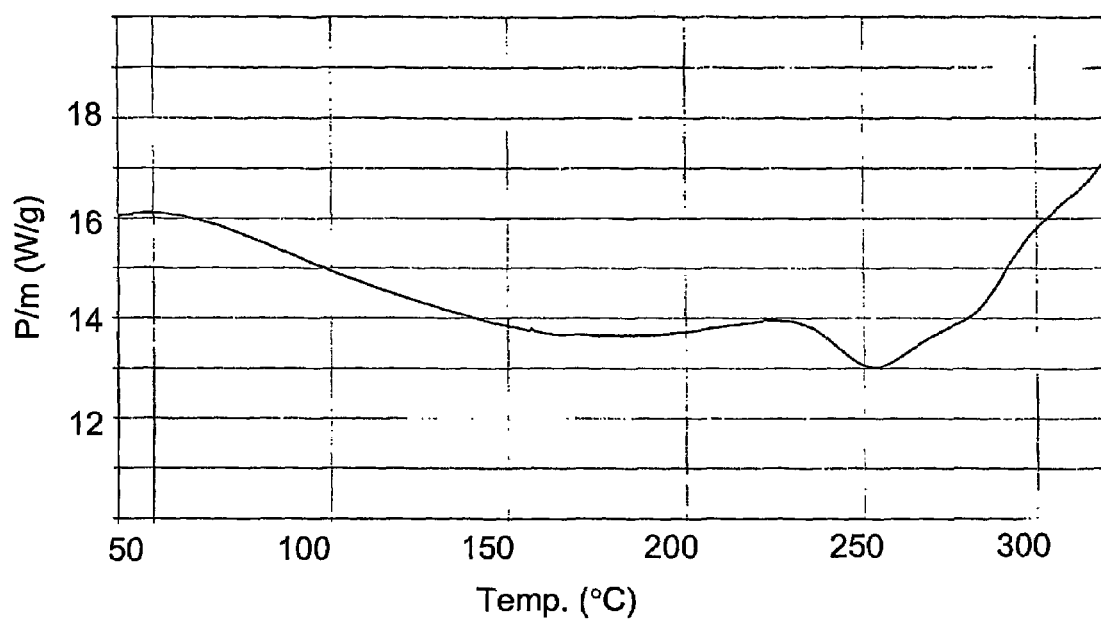
FIG. 6: DSC thermogram of calcium salt of losartan
Figure 7:
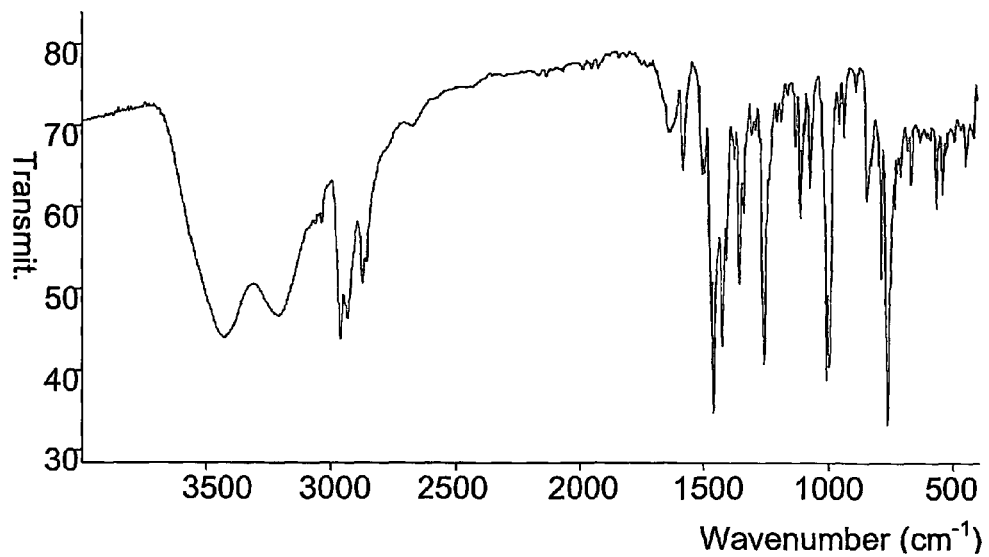
FIG. 7: IR spectrum of crystalline potassium salt of losartan (Form I)
Figure 8:
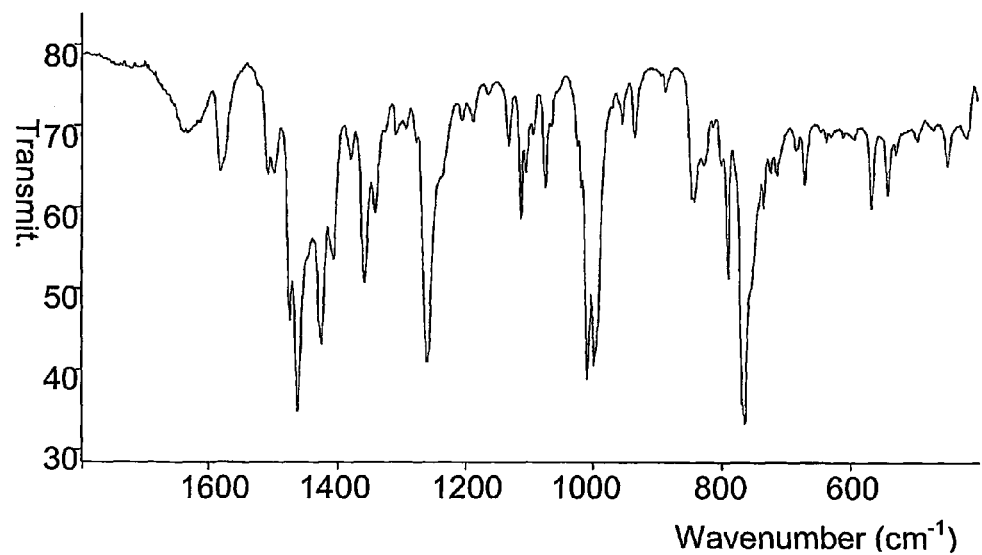
FIG. 8: Enlargement of part of IR spectrum of FIG. 7
FIG. 9: IR spectrum of amorphous potassium salt of losartan
Figure 9:
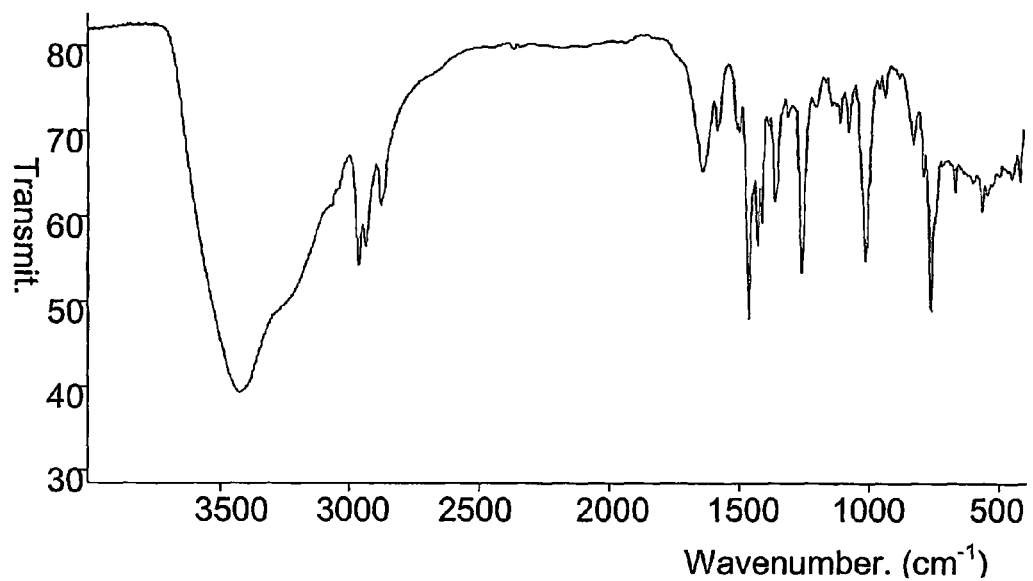
Figure 10:
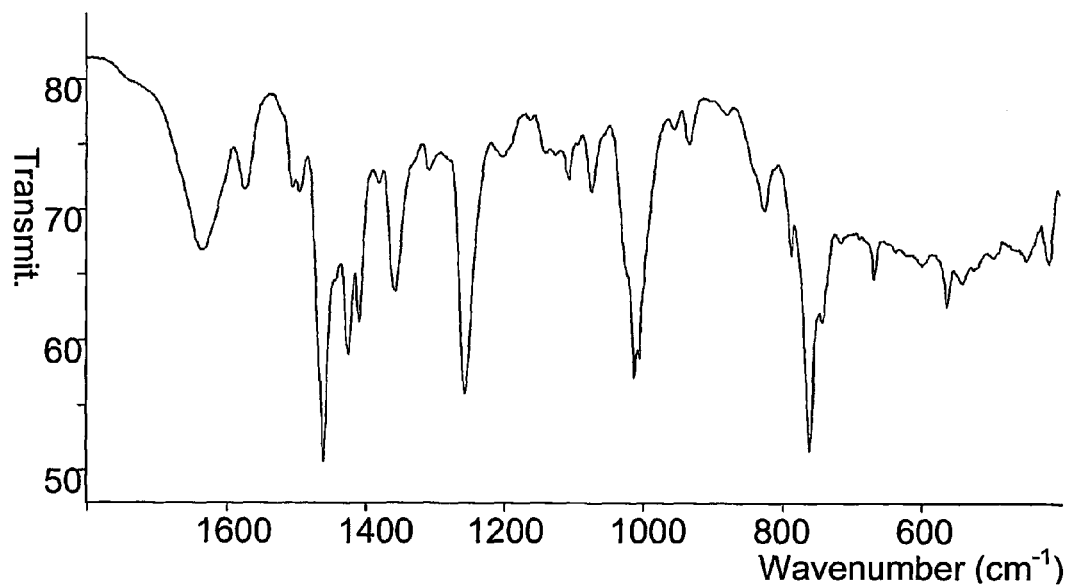
FIG. 10: Enlargement of part of IR spectrum of FIG. 9
FIG. 11: IR spectrum of crystalline sodium salt of losartan
Figure 11:
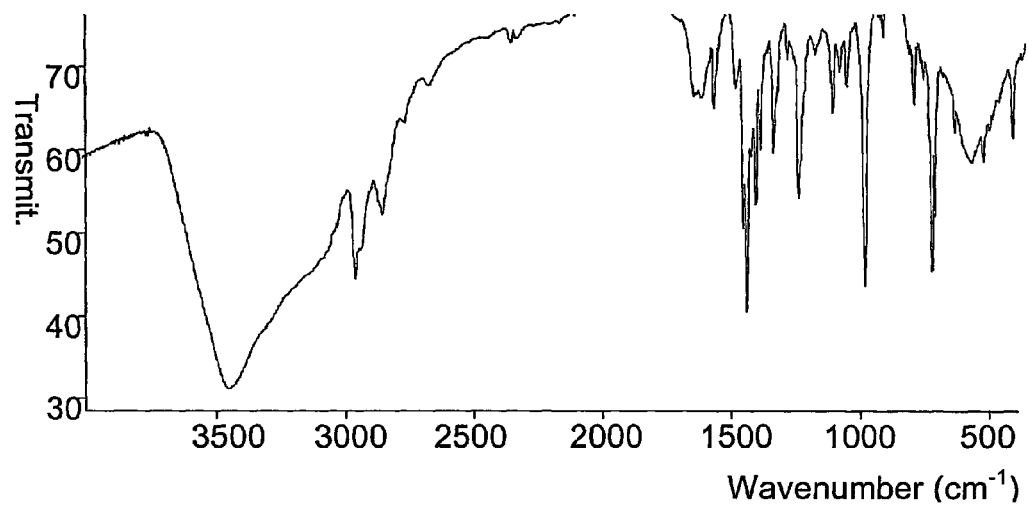
Figure 12:
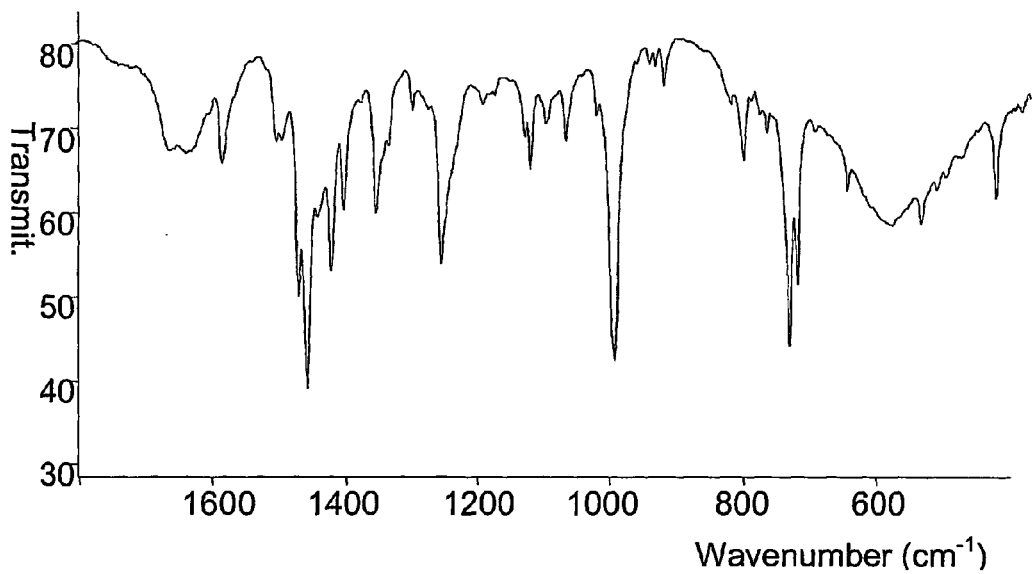
FIG. 12: Enlargement of part of IR spectrum of FIG. 11
FIG. 13: IR spectrum of amorphous sodium salt of losartan
Figure 13:
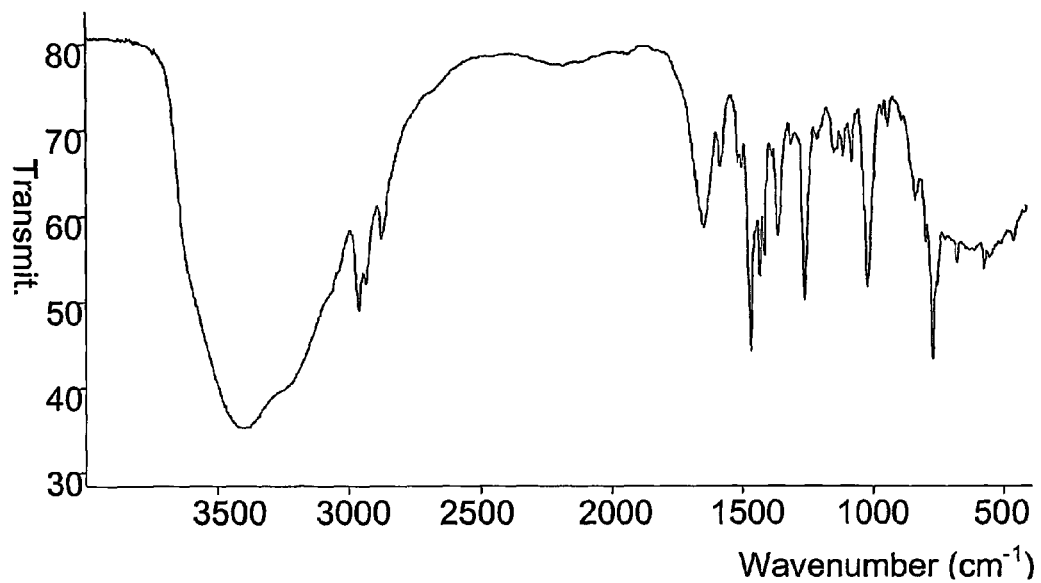
Figure 14:
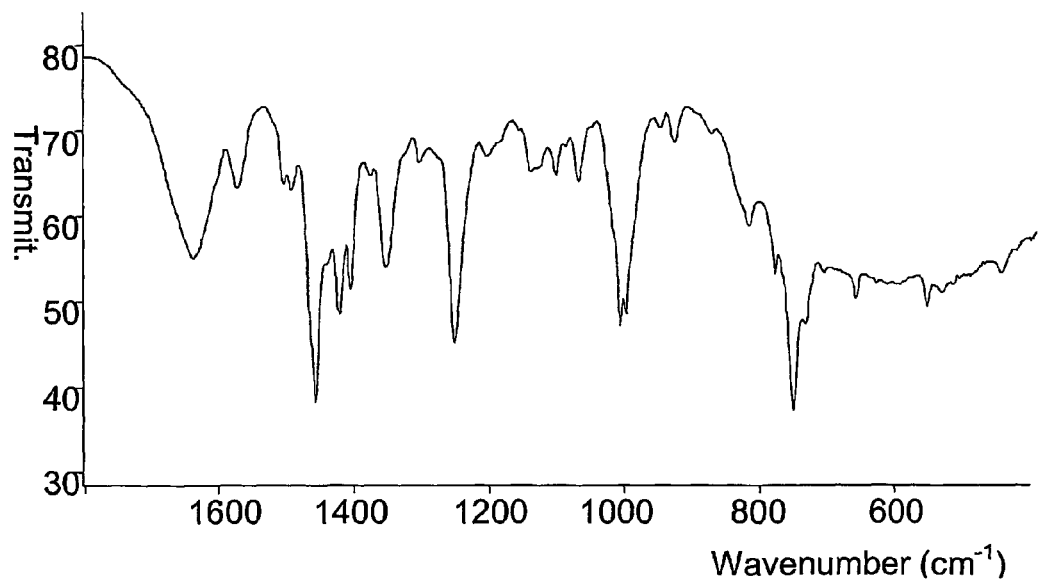
FIG. 14: Enlargement of part of IR spectrum of FIG. 13
FIG. 15: IR spectrum of magnesium salt of losartan
Figure 15:
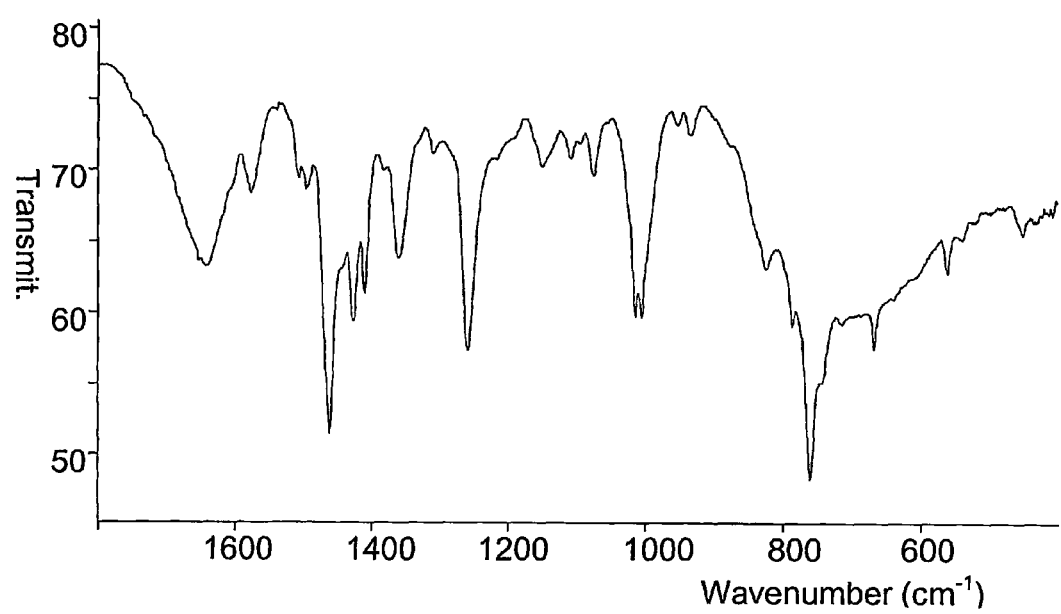
Figure 16:
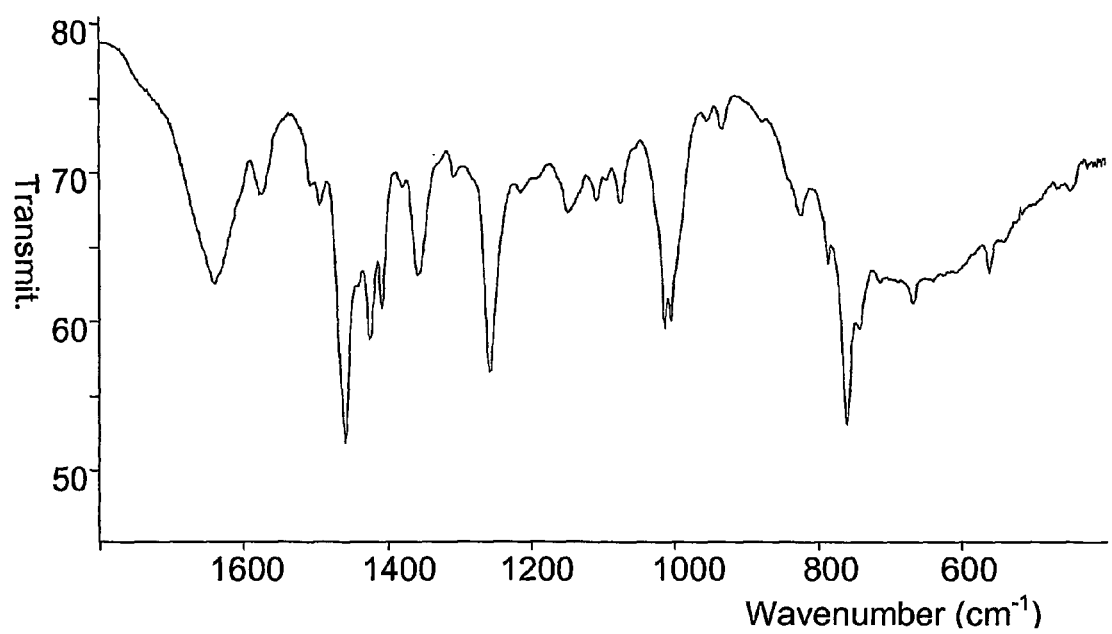
FIG. 16: IR spectrum of calcium salt of losartan
Figure 17:
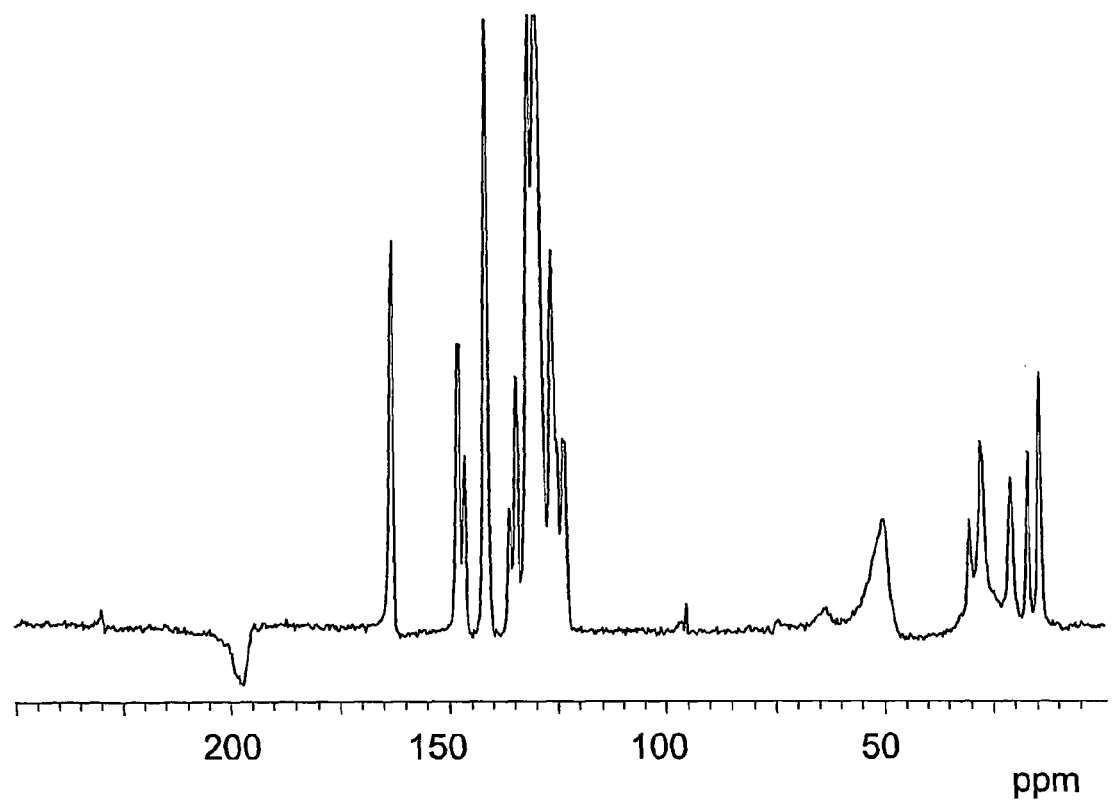
FIG. 17: $^{13}$C CP/MAS NMR measurement of a sample of crystalline potassium salt of losartan (Form I)
Figure 18:
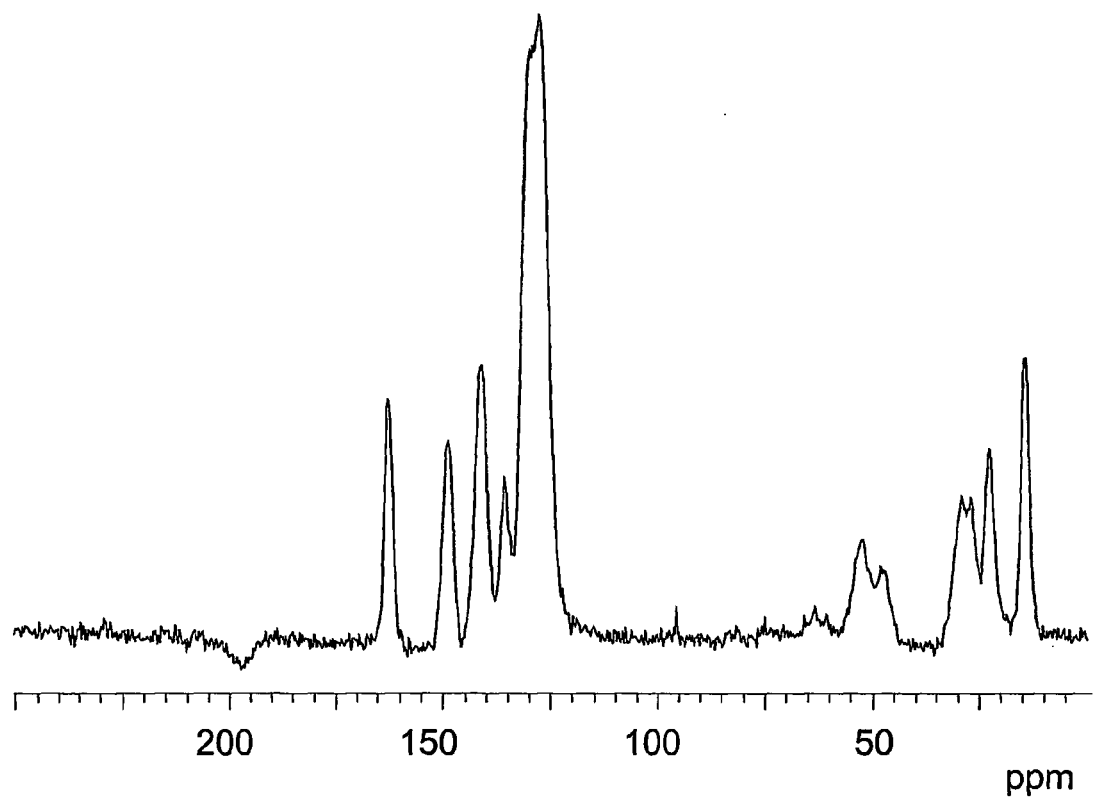
FIG. 18: $^{13}$C CP/MAS NMR measurement of a sample of amorphous potassium salt of losartan
Figure 19:
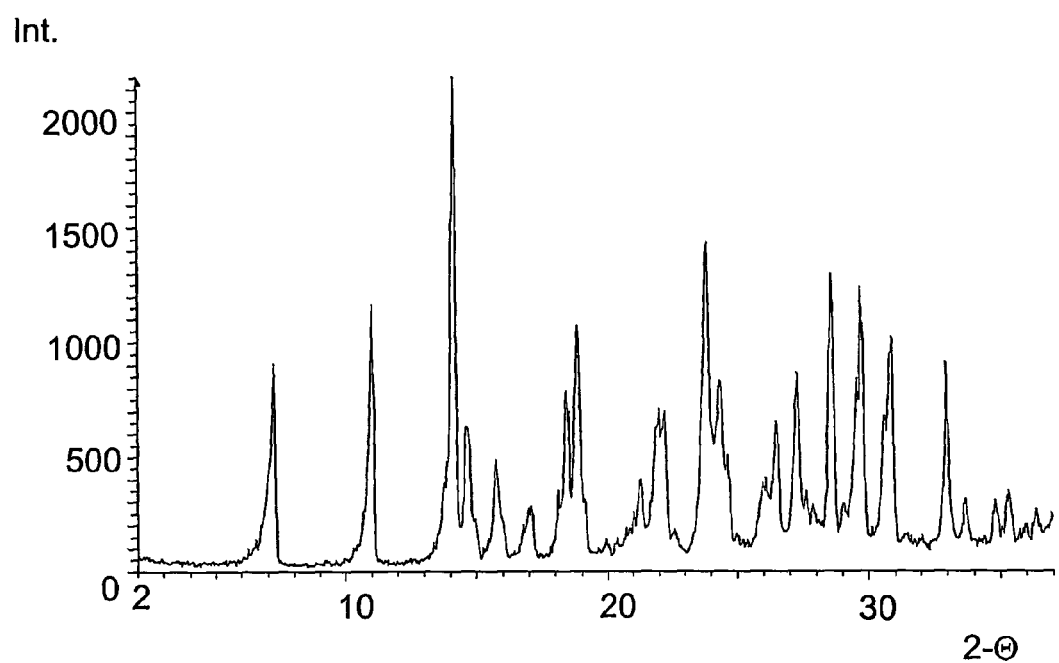
FIG. 19: X-ray powder diffraction pattern of crystalline potassium salt of losartan (Form I)
FIG. 20 X-ray powder diffraction pattern of amorphous potassium salt of losartan
Figure 20:
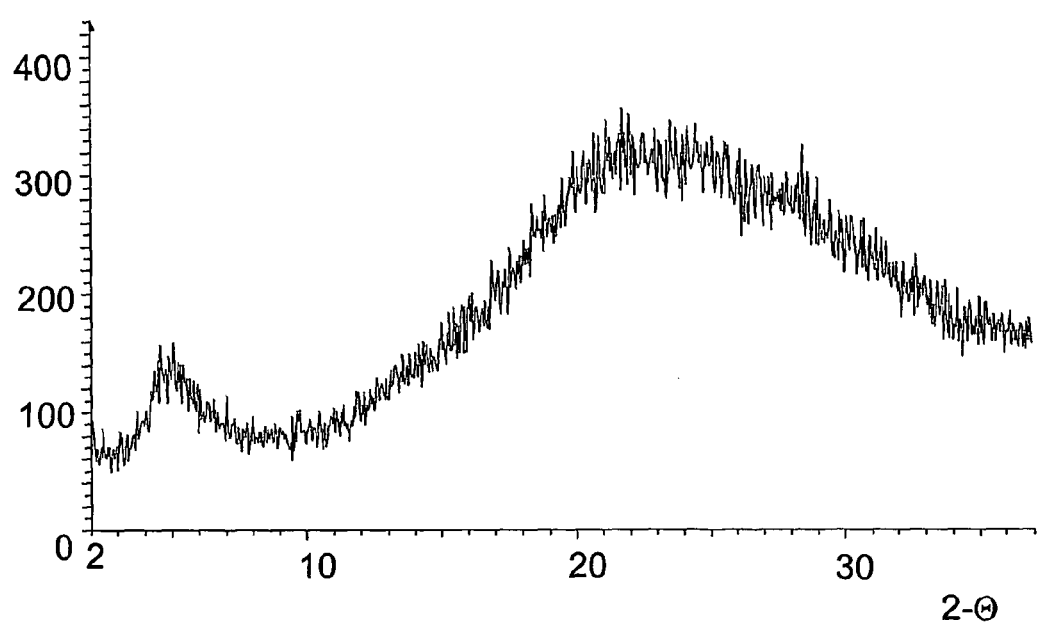

Present invention describes formation of novel alkali and earth-alkali salts of 2-n-butyl-4-chloro-5-hidroxymethyl-1-[[2'-(1H-tetrazole-5-yl)[1,1'-biphenyl]-4-yl]-1H-imidazole and polymorph forms thereof, particularly novel forms of potassium salt of 2-n-butyl-4-chloro-5-hidroxymethyl-1-[[2'-(1H-tetrazole-5-yl)[1,1'-biphenyl]4-yl]-1H-imidazole, i.e., losartan potassium. Present invention further describes purification of those compounds and pharmaceutical compositions into which they are formulated.

To prepare quality salts suitable for pharmaceutical use one needs amphoteric losartan of high purity. This particularly applies to preparation of amorphous salts, because amorphisation, i.e., lyophilisation, cannot yield a substance of higher purity. For the preparation of high quality losartan or potassium salt of losartan we have discovered that an effective purification can be reached by transition amphoter—alkali or earth-alkali salt—amphoter without separate purification of intermediates. Processes through different salts give different levels of purification, most effective are processes via potassium or sodium salts which form in the solvents as crystalline salts.

The process for preparing losartan potassium, which is one embodiment of present invention, has a definite advantage over the prior art, because losartan potassium purified via said two salts has proved more pure than losartan potassium prepared according to the teaching of WO 9310106, which does not yield a substance of pharmaceutical quality, however, the above application gives no process which would additionally purify the product.

Purification via sodium as well as potassium salt is an effective method because very pure losartan was gained, from which we were able to prepare more pure losartan potassium than described in the prior art.

Surprisingly, the method via sodium salt is more robust due to much lower effect of pH on the yield and, further, the yield via sodium salt exceeds the yield via potassium salt as shown in Table 1.

TABLE 1

Comparison of yield and purity of losartan purified via different salts

| | purification | | | | | |
| --- | --- | --- | --- | --- | --- | --- |
| | via Na salt | | via K salt | | via Ca salt | |
| phase | purity | yield | purity | yield | purity | yield |
| crude losartan | 98.44% | | 98.44% | | 98.44% | |
| salt | 99.42% | 82% | 99.67% | 77% | 98.16% | 91.9% |
| losartan | 99.74% | 94% | 99.82% | 93% | 98.98% | 91.0% |
| losartan K | 99.91% | 94% | 99.88% | 96% | 99.81% | 88.9% |

In this transition the substance is effectively purified, and the obtained amphoteric losartan has a low level of impurities, and is suitable for preparing crystalline or amorphous potassium salts for pharmaceutical use. Such amphoteric substance can also be worked up into quality alkali or earth-alkali salts of losartan.

Specifically, the embodiments of the invention are: earth-alkali salts of losartan, preferably chosen from magnesium or calcium salt, and alkali salts of losartan, preferably sodium salt of losartan.

In one embodiment of the invention the sodium salt of losartan is characterized by being in crystalline form, and is characterized by a powder X-ray diffraction pattern with peaks at about $2\theta=6.2°$, $14.5°$, $18.2°$, $18.8°$, $21.6°$, $23.5°$, $24.8°$ and $25.5°$.

When mentioning the peaks that were read-out from the powder X-ray diffractions pattern (which we have recorded), around $2\theta=n°$ or about $2\theta=n°$ means $n\pm0.2°$, preferably $n\pm0.1°$, and it is understood that the exact values of diffractions in the difractogram depend on the X-ray diffraction measuring equipment and temperature.

Figure 21:
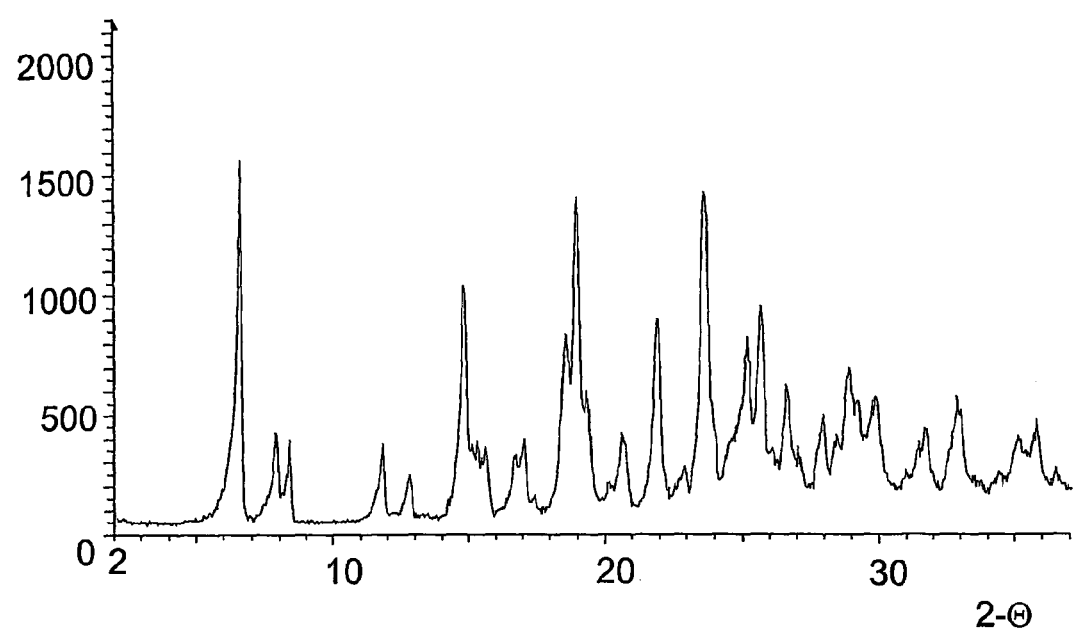
FIG. 21: X-ray powder diffraction pattern of crystalline sodium salt of losartan
Figure 22:
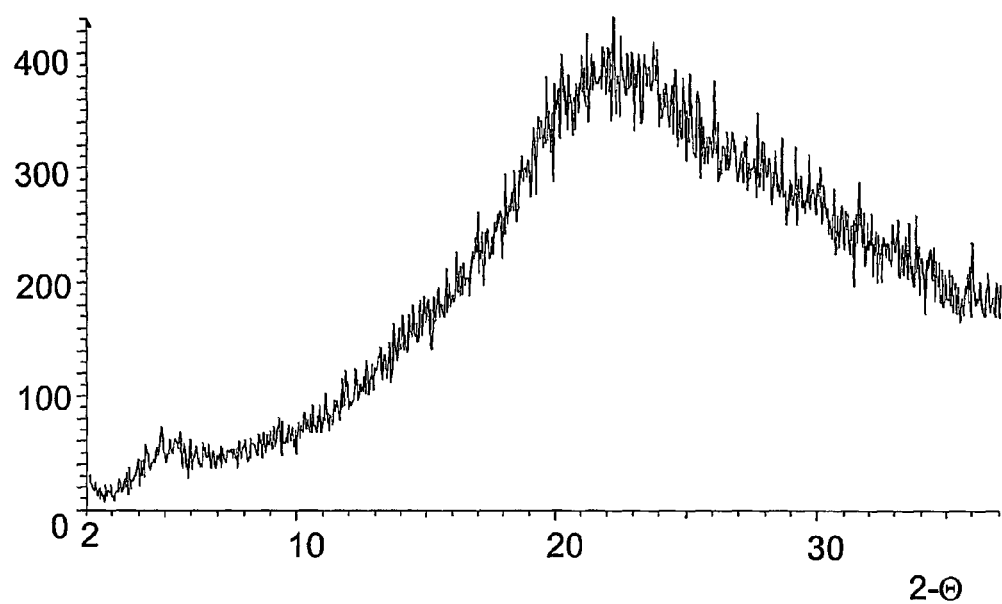
FIG. 22: X-ray powder diffraction pattern of amorphous sodium salt of losartan
Figure 23:
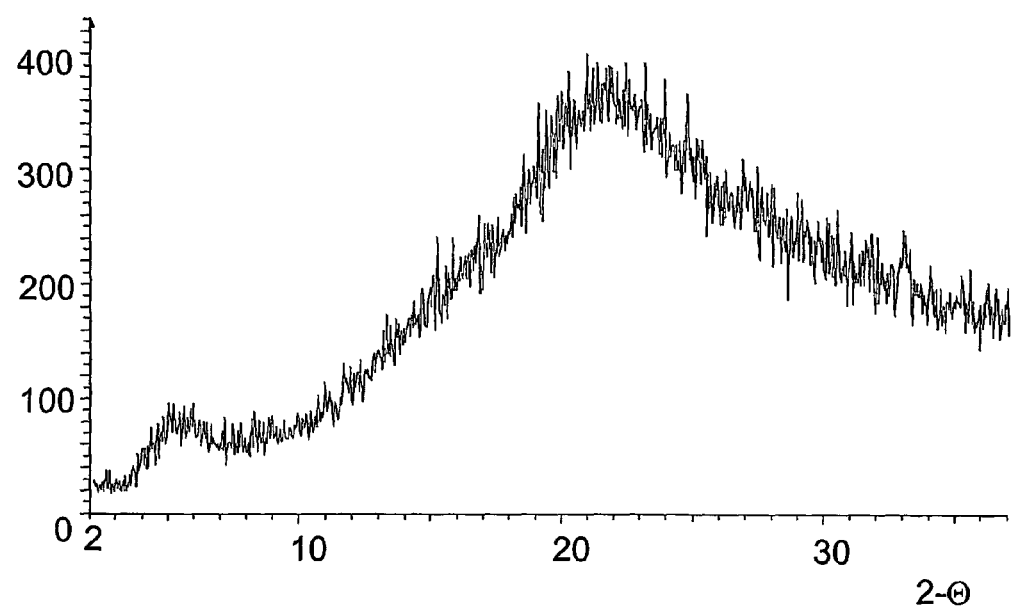
FIG. 23: X-ray powder diffraction pattern of magnesium salt of losartan
Figure 24:
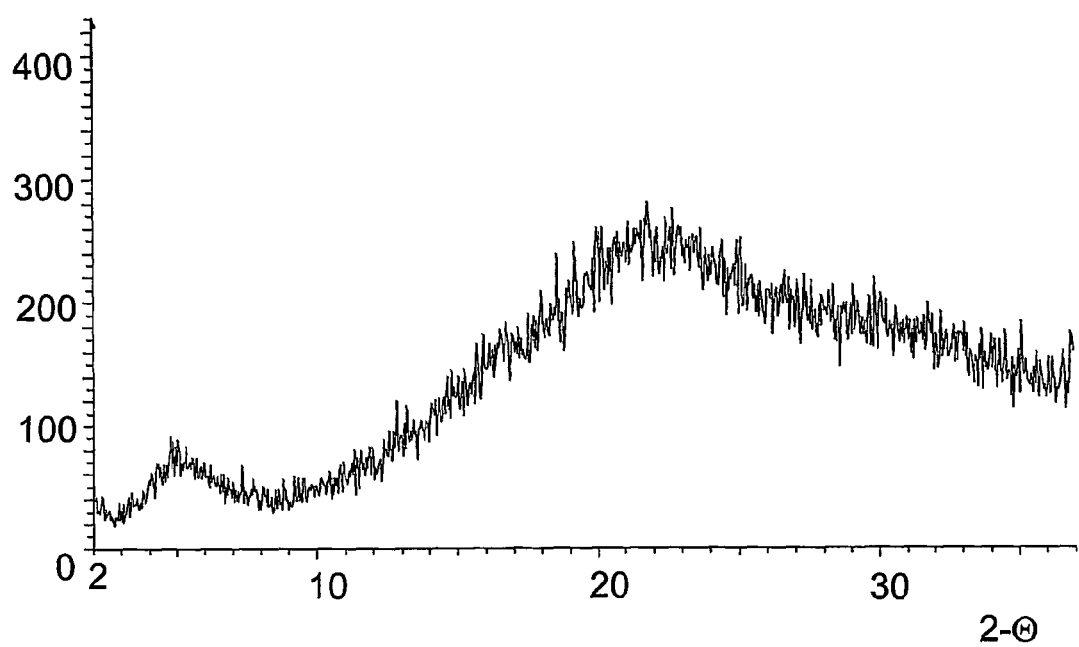
FIG. 24: X-ray powder diffraction pattern of calcium salt of losartan
Figure 25:
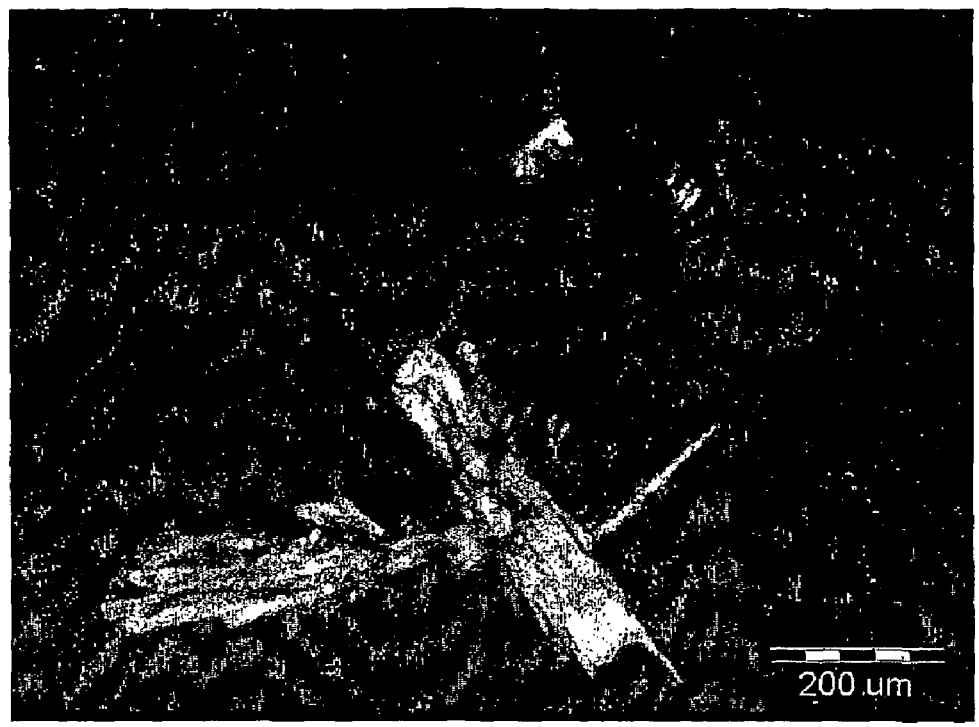
FIG. 25: Photograph of a crystal of crystalline form with bound water of potassium salt of losartan

In another embodiment the sodium salt of losartan is characterized by a powder X-ray diffraction pattern essentially as depicted in FIG. 21, and further characterized by being in crystalline form and having a melting point between 190 and 200° C., and yet further characterized in that it is in crystalline form with bound water, in which the water content is between around 3.5% and around 4.5% by weight, and the water is lost while drying between around 100 and around 120° C.

Another embodiment of the invention represent alkali or earth-alkali salts of losartan in amorphous form, preferably amorphous potassium, calcium, magnesium, and sodium salt of losartan.

In one aspect, the present invention is a process for preparing alkali or earth-alkali salts of losartan characterized by a process comprising the following steps: adding to the solution of losartan in an alcohol or a mixture comprising alcohol and aprotic solvent an alcoholate of an alkali or an earth-alkali metal; precipitating or crystallizing the obtained salt; and isolating the obtained precipitated or crystallized salt by filtration or centrifugation; preferably, when earth-alkali salt is chosen from magnesium or calcium salt; alkali salt is chosen from potassium or sodium salt, more preferably, a process characterized in that the alcoholate is chosen from sodium or potassium t-butanolate, more preferably, a process characterized in that the alcohol is i-propanol, more preferably, a process characterized in that the alkali or earth-alkali salt is precipitated or crystallized by addition of an aprotic solvent.

In another aspect, present invention is a process for preparing sodium salt of losartan characterized by the following steps: adding to the solution of losartan a solution of sodium hydroxide until the pH lies between around 9 and around 12; precipitating or crystallizing the obtained salt by addition of an aprotic solvent; and isolating the obtained precipitated or crystallized salt by filtration or centrifugation; preferably, a process characterized in that the aprotic solvent is n-heptan.

In another aspect, the present invention is a process for the purification of losartan, characterized by the following steps: conversion of losartan into a salt; subsequent isolation of said salt; conversion of said isolated salt into losartan.

Preferably, the invention is in one aspect a process of purifying losartan, characterized by comprising the following steps: preparing an alkali or an earth-alkali salt of losartan as described above or preparing a sodium salt as described above; and preparing losartan from obtained isolated salt by acidifying with an inorganic acid in an organic solvent, more preferably, a process characterized in that the alkali salt is chosen from sodium or potassium salt, and that said salt is isolated in crystalline form, and that preparing losartan from obtained isolated salt by acidifying with an inorganic acid in an organic solvent consists of the following steps: dissolving the isolated salt in water or mixture of water and an organic solvent; adding to the obtained solution an inorganic acid until the pH lies between around 3.6 and around 3.8; cooling the obtained solution under around 10° C. when the losartan precipitates or crystallizes; and subsequent digesting of obtained precipitated or crystallized losartan with an organic solvent, more preferably, a process according to which an inorganic acid is sulphuric acid and, most preferably, a process according to which an organic solvent is ethyl acetate. Digesting with a solvent as used in this patent application means to suspend in a solvent while mixing.

In one embodiment, present invention provides a process for preparing amorphous potassium salt of losartan by removing water by drying a potassium salt of losartan in crystalline form with bound water, preferably from dihydrate or form comprising up to around 12% of bound water.

In yet another aspect, present invention is a process for preparing alkali or earth-alkali salt of losartan in amorphous form, wherein said alkali salt is a sodium salt of losartan and earth-alkali salt is chosen among calcium salt and magnesium salt, preferably, a process characterized in that the last step of the process comprises lyophilisation of frozen aqueous solution of alkali or earth alkali salt of losartan, more preferably, a process characterized by comprising the following two steps: freezing the solution of alkali or earth-alkali salt of losartan; lyophilising the obtained frozen solution.

In yet another aspect, present invention relates to a process for preparing alkali or earth-alkali salt of losartan in amorphous form from losartan, comprising the following steps: suspending losartan in water; dissolving the obtained suspension by adding an aqueous solution of alkali metal hydroxide or alcoholate or earth-alkali metal hydroxide or alcoholate at a temperature above 0° C. until the pH of the solution reaches at least about 9.3; freezing the obtained solution of salt of losartan; and lyophilising the obtained frozen solution.

In yet another aspect, present invention relates to a process preparing a potassium salt of losartan in amorphous form from losartan, comprising the following steps: suspending losartan in water; dissolving the obtained suspension by adding an aqueous solution of potassium hydroxide at a temperature between about 0 and about 30° C. until the pH of the solution has reached at least about 9.3; freezing the obtained solution of potassium salt of losartan; and lyophilizing the obtained frozen solution, more preferably, to a process, wherein alkali or earth-alkali salt of losartan in amorphous form is prepared from losartan, which has been purified by a process comprising the following steps: conversion of losartan into its salt; subsequent isolation of named salt; and transformation of isolated salt into losartan, more preferably, to a process wherein alkali or earth-alkali salt of losartan in amorphous form is prepared from losartan, which has been purified by a process comprising the following steps: transforming losartan into alkali or earth alkali salt of losartan; isolating the obtained salt; and transforming the obtained isolated salt into losartan by acidifying with inorganic acid in an organic solvent, more preferably, to a process wherein alkali or earth-alkali salt of losartan in amorphous form is prepared from losartan, which has been purified by a process comprising the following steps: transforming losartan into potassium or sodium salt of losartan; isolating the obtained salt in crystalline form; dissolving the obtained isolated salt in water, or a mixture of water and organic solvent; adding to the obtained solution an inorganic acid until a pH between around 3.6 and around 3.8; cooling the obtained solution under around 10° C. so that losartan forms in a solution as a solid; and digesting the obtained losartan by an organic solvent, more preferably, to a process wherein potassium salt of losartan in amorphous form is prepared from losartan, which has been purified by a process comprising the following steps: transforming losartan into potassium or sodium salt of losartan; isolating the obtained salt in crystalline form; dissolving the obtained isolated salt in water or a mixture of water and organic solvent; adding to the obtained solution an inorganic acid until a pH between around 3.6 and around 3.8; cooling the obtained solution under around 10° C. so that losartan precipitates; and digesting gained losartan by an organic solvent, yet, more preferably, to a process wherein the transformation of losartan into potassium salt and isolation thereof within the purification process are characterized by the following steps: adding potassium alcoholate to a solution of losartan in an alcohol, or a mixture comprising alcohol and aprotic solvent; precipitating or crystallizing the obtained salt; isolating the obtained precipitated or crystallized salt by filtration or centrifugation, yet, more preferably, to a process, wherein transformation of losartan into sodium salt and isolation thereof within the purification process are characterized by the following steps: adding to the solution of losartan in an alcohol, or a mixture comprising alcohol and an aprotic solvent, a sodium alcoholate or a sodium hydroxide until a pH between around 9 and around 12; precipitating or crystallizing the obtained salt; isolating the obtained precipitated or crystallized salt by filtration or centrifugation, yet, more preferably, to a process, wherein said inorganic acid is sulphuric (VI) acid, and to a process wherein the organic solvent is ethyl acetate.

Aspects of the invention are also the use of alkali or earth-alkali salt of losartan in the process of purifying losartan as described above, preferably, use of a crystalline sodium salt of losartan, and use of isolated crystalline alkali or earth-alkali salt of losartan in the process for preparing an alkali or earth-alkali salt of losartan in amorphous form, preferably, use of isolated crystalline sodium salt of losartan in the process for preparing potassium salt of losartan in amorphous form.

In one embodiment of the invention, crude losartan was purified according to the following procedure: losartan dissolved in alcohol was transformed into potassium or sodium salt, the obtained salt was isolated in crystalline form, the obtained isolated crystalline salt was dissolved in water, or a mixture of water and at least one organic solvent, to the obtained solution an inorganic acid was added until a pH around 3.6 and 3.8 was reached, the obtained solution was cooled under around 10° C., when losartan precipitated or crystallized. In such manner the obtained losartan was further digested with an organic solvent.

From losartan purified in described manner, losartan potassium can be prepared by known procedures, e.g., by adding a solution of NaOH. In an analogous manner, other alkali or earth-alkali salts of losartan can be prepared, which have substantially less impurities than in the case when they are prepared from amphoteric losartan isolated directly from a synthesis. Such salts are suitable for galenic use.

In the process of purifying losartan by transition amphoter-alkali salt or earth-alkali salt—amphoter there are two sub-processes: namely, the preparation of salt and isolation thereof, and subsequent preparation of amphoter from said salt.

Preparing Alkali or Earth-Alkali Salt of Losartan and Isolation thereof.

We have discovered that in accordance with the first part of the process, alkali or earth-alkali salts of losartan could be prepared if losartan was dissolved in a suitable solvent, e.g., alcohol, or a mixture of alcohol and an aprotic solvent, preferably in isopropanol in a manner that concentration of losartan was around 170 g/l, whereupon there was added an aqueous solution of hydroxide of an alkali or earth-alkali metal at temperature between around 38° C. and around 40° C. until a pH between around 9 and around 12.5, preferably around 10, during around 15 min to around 1 hour, preferably during half an hour, whereupon it was distilled until the entire azeotropic mixture was removed.

The process for preparing earth-alkali salts of losartan was researched in detail, and same were prepared by adding anhydrous alcoholate of an earth-alkali metal to a solution of losartan in a suitable solvent, or mixture of solvents, e.g., in isopropanol in which the concentration of losartan was around 170 g/l. The reaction mixture was stirred at an elevated temperature between around 40° C. and around 85° C., preferably at reflux temperature.

In all cases, we have precipitated alkali or earth alkali salts of losartan thus prepared from the solutions in isopropanol with a non-polar solvent, preferably n-heptane, at low temperature, preferably, at temperatures below around 10° C., and isolated same according to known procedures. The result of such preparation are crystalline sodium and potassium salt and, surprisingly, amorphous magnesium and calcium salt. Crystalline potassium salt is a known form, and was shown to be Form I, while sodium salt has not yet been characterized.

Surprisingly, it was discovered that crystals of sodium salt of losartan are bigger and formed better provided the mixture of solvents from which they crystallize contained some water. In one embodiment of present invention, salts of losartan can be prepared also in a form with bound water, which can be influenced by choosing the conditions, e.g., the pH. Crystalline sodium salt of losartan prepared at a pH around 12 retains between around 3.5% and around 4.5% water after drying, and does not release water until after having been heated over around 100° C.

Preparing magnesium salt with magnesium alcoholate, e.g., magnesium ethanolate, is preferred because use of magnesium hydroxide is not practical (due of its low solubility and conversion into magnesium oxide, which is not soluble). Surprisingly, we have discovered that better results, better yields as well as higher quality can be attained by using sodium or potassium alcoholates in non-aqueous media, e.g., alcohol, instead of using aqueous solution of NaOH or KOH. The process is also shorter because it does not require removing of water by azeotropic distillation. The solution of potassium or sodium alcoholate can be prepared by dissolving commercially obtainable sodium or potassium t-butanolate. The solution of sodium alcoholate can be prepared by adding sodium to alcohol, which must be carried out prior to adding losartan, while potassium t-butanolate can be added directly to the solution of losartan in alcohol. The yield using known method with a hydroxide is sensitive to pH and the presence of water; these two factors do not significantly apply to the method using aloholates.

The most preferred process for preparing losartan potassium is the following: Losartan is dissolved in a suitable solvent, e.g., alcohol, preferably isopropanol, so that the concentration is around 370 g/l, whereupon after adding potassium t-butanolate, potassium salt separates. By adding a non-polar solvent, e.g., hydrocarbon, preferably n-heptane, separation of the solid salt from the solution increases. Losartan potassium is isolated by simple filtering and drying. In an analogous manner, also sodium salt is prepared by using sodium t-butanolate.

Preparing Losartan from its Alkali or Earth-Alkali Salt

In accordance with the second part of the process amphoter-salt-amphoter, the salt prepared according to one of the described procedures was dissolved in around 5 to around 20 times the amount of water, preferably at a concentration around 100 g/l and at a temperature from around 5° C. to around 25° C., preferably in an interval from 21° C. to 25° C. Then an organic solvent, preferably ethyl acetate, was added, and reaction mixture was acidified with inorganic acid, preferably concentrated inorganic acid, most preferably, sulphuric (VI) acid until a pH between around 3.6 and around 3.8, most preferably, until a pH around 3.7, whereupon the reaction mixture was cooled to a temperature around 0° C. to around 10° C., preferably below 10° C., and losartan was isolated by known procedures.

Preparing Amorphous Forms of Alkali and Earth-Alkali Salts of Losartan

We have discovered and confirmed with X-ray analysis that magnesium and calcium salts obtained according to described process are amorphous. On the other hand, isolated potassium salt obtained according to the process as described, is the known crystalline Form I, while sodium salt not known until now, is also crystalline. Thus a method of precipitating salts of losartan from alcohol or a mixture of alcohol and other organic solvent cannot be a general method for preparing amorphous salts.

In another embodiment of the invention, a preparation of completely amorphous alkali or earth-alkali salts of losartan without added pharmaceutically acceptable other substances is described. It was, surprisingly, discovered that by lyophilisation of aqueous solution of alkali or earth-alkali salt of losartan, an active ingredient in a form of fine amorphous powder is obtained. By this short and robust method, without lengthy and strictly controlled crystallization process, in a simple manner, losartan potassium for incorporation into a pharmaceutical composition was obtained. In some instances, the amorphous form has a better bio-availability than the crystalline forms as evident from celecoxib examples mentioned [WO 01422221], or some examples from U.S. Ser. No. 65/284,277. By having water as a solvent in the end phase of isolation, there was also solved the problem of undesired residual solvents.

In one embodiment of present invention, we have prepared amorphous potassium salt of losartan from crude losartan according to the following procedure: losartan was first purified in a process comprising the following steps: losartan dissolved in alcohol was transformed into a potassium salt of losartan, the obtained salt was isolated in crystalline form, the obtained isolated salt was dissolved in water, or a mixture of water, and at least one organic solvent, to the obtained solution an inorganic acid was added until a pH between around 3.6 and 3.8, the obtained solution was cooled under around 10° C. when losartan precipitated or crystallized. In this manner, losartan as obtained was further digested with an organic solvent; further amorphous losartan potassium was prepared by suspending purified losartan in water, and subsequently dissolving the obtained suspension by adding aqueous solution of potassium hydroxide at a temperature from 0° C. to 30° C. until a pH of the solution has reached a pH between around 9 and around 10, preferably at least 9.3; freezing the obtained solution and, in the last step, lyophilising the obtained frozen solution, i.e., drying under lowered pressure, preferably between around 0.1 and around 0.01 bar.

In the case that pharmaceutically suitable and sufficiently pure alkali or earth-alkali salts of losartan are available, amorphous forms thereof can be prepared in simple manner by lyophilising frozen aqueous solutions thereof.

Preparing Novel Crystalline Form with Bound Water of Losartan Potassium

In an embodiment, present invention provides a process for preparing a novel crystalline form with bound water of losartan potassium. An essential feature of the described process is the presence of water.

It is possible to form a new crystalline form with bound water from amorphous losartan potassium in moist atmosphere. The amorphous substance is hygroscopic and it binds water, during this process the system transforms into a crystalline structure, which, e.g., proceeds at room temperature at 80% relative humidity or at a 60% relative humidity already.

A form comprising from 12 to 16% water can be isolated according to the teaching of WO 03048135 with exposure of amorphous or Form I losartan potassium to atmospheric moisture. According to present invention, a crystalline form was prepared containing from around 7% to around 12% water from a combination of solvents and water, as well as by exposure to humid air.

In further studies of a new crystalline structure with bound water, there was, surprisingly, discovered that losartan potassium in said form was less soluble than known Form I, or amorphous losartan potassium, therefore it forms as a solid from the solution prepared by dissolving losartan potassium in a small volume of water, in which the mass of water is from 0.4 to 1.2 times the mass of losartan. From hardened solid thus formed, losartan potassium is obtained by drying and milling or grinding.

Technologically it is more advantageous if the solid is isolated by filtering or centrifuging as compared to milling or grinding a hardened solid, therefore, in another embodiment of the invention, there was to the thick water suspension added a solvent, or a mixture of solvent, which does not mix, or only poorly mixes with water, which caused the thick suspension to dissolve and become less dense so that it could be easily filtered or centrifuged.

Under certain conditions, losartan potassium converts into a new crystalline structure with bound water under intensive stirring in a mixture of non-polar hydrophobic solvent and water or, provided that a small amount of water is added to the suspension of losartan potassium in such solvent or, provided that to the saturated aqueous solution of losartan potassium, a solvent or a mixture of solvent is added which does not mix or poorly mixes with water.

In the case that the solvent mixture contains a comparatively great amount of water, losartan potassium will dissolve; if the amount of water is not sufficient, the conversion is not complete, or is too slow. We have, surprisingly, discovered that in one embodiment of the invention, there can, optimally, be isolated a new crystalline structure with bound water when the ratio of the amount of water as compared to the amount of losartan is only a 3.6 molar ratio (0.14 weight ratio).

Solvents combined with an adequate molar amount of water from which a new crystalline structure with bound water can be isolated, e.g., include: ethers non-miscible with water (diethyl ether, diisopropyl ether, t-butyl methyl ether), hydrocarbons (alkanes, such as: pentane, hexane, heptane; alkenes), cyclic hydrocarbons (cyclohexane, methylcyclohexane), aromatic hydrocarbons (benzene, toluene, xylene), esters (ethyl acetate, isopropyl acetate, n-butyl acetate), as well as combinations thereof.

New crystalline structure with bound water can also be prepared from known Form II, however the conversion can be slower or incomplete due to lower solubility in water.

It was possible to successfully convert losartan potassium into new crystalline structure with bound water in solvents comprising from 0.11 to 1.2 times the weight surplus of water according to the weight of losartan.

The most preferable process for preparing a new crystalline structure with bound water is, as follows: Potassium salt of losartan is suspended in diethyl ether, water is under intensive stirring added to the suspension at room temperature. The molar surplus of water to losartan is from around 3 to around 30, preferably from around 3 to around 12. The suspension is stirred overnight, and the formed crystalline solid is filtered and dried. In the case that solvents or a mixture of solvent are used, which poorly mix with water, the molar ratio is preferably closer to 3.

In an important embodiment of the invention, a new crystalline form of potassium salt of losartan with bound water is provided, characterized by strongest diffractions in powder X-ray difractogram at around $2\theta=13.0$, 17.2, 19.7, 20.9, 21.0, 23.2, 23.6, 24.5, 25.0, 26.6, 17.3, 28.2, 29.0, 31.5°, for which we use the name crystalline form with bound water.

It is characteristic for new crystalline form of potassium salt of losartan with bound water to comprise bound between about 7% and about 13% water. While performing thermogravimetric analysis of the sample following occurred: water was lost in two steps, in first step while heating until around 55° C. sample lost around 4% of mass in subsequent step around 8%, together around 12%. While heating above around 120° C. sample did not loss any mass until substantial decomposition.

Therefore, in an aspect, present invention provides a potassium salt of losartan in crystalline form with bound water, characterized by a powder X-ray diffraction pattern with peaks at about $2\theta=13.0$, 17.2, 19.7, 20.9, 21.0, 23.2, 23.6, 24.5, 25.0, 26.6, 17.3, 28.2, 29.0, 31.5° where the water content is between around 7% and 12% by weight, preferably to potassium salt of losartan in crystalline form, with bound water as described above, characterized in that it is crystallized as a dihydrate and preferably to potassium salt of losartan in crystalline form, with bound water as described above, characterized by a loss of mass of around 4% by weight while heating up to around 55° C., and subsequent loss of around 8% by weight while heating above 55° C. up to around 120° C.

In yet another aspect, the present invention is a process for preparing a potassium salt of losartan in crystalline form with bound water as described above, characterized by conversion of potassium salt of losartan in the presence of water, preferably a process characterized by comprising the following steps: preparing a concentrated aqueous solution of potassium salt of losartan wherein the mass of water is from about 0.4 to about 1.2 times the mass of losartan; and isolating a potassium salt of losartan in crystalline form by drying and milling.

In yet another aspect, the present invention is a process for preparing a potassium salt of losartan in crystalline form with bound water as described above, characterized by water being present as moisture, preferably characterized by preparation from amorphous potassium salt of losartan by exposing same to an atmosphere having a relative humidity from about 20% to about 60%.

In yet another aspect, present invention is a process for preparing a potassium salt of losartan in crystalline form with bound water, characterized by water being present in the mixture with one or several solvents, which do not mix with water, or poorly mix with water, preferably a process, characterized by comprising the following steps: preparing a concentrated aqueous solution of potassium salt of losartan wherein the mass of water is from about 0.4 to about 1.2 times the mass of losartan; adding to the obtained aqueous solution one or several solvents, which do not mix with water or poorly mix with water; and isolating potassium salt of losartan in crystalline form from the obtained mixture of solvents, more preferably, a process, characterized by comprising the following steps: preparing a suspension of potassium salt of losartan in a mixture of water and at least one solvent, which does not mix with water or poorly mixes with water, wherein the molar ratio of water and losartan is from about 3 to about 30; and isolating a potassium salt of losartan in crystalline form from the obtained mixture of solvents, more preferably, a process wherein the solvent, which does not mix with water or poorly mixes with water, is chosen from: dietyl ether, diisopropyl ether, butyl methyl ether, pentane, hexane, heptane, cyclohexane, methylcyclo hexane, benzene, toluene, xylene, ethyl acetate, propyl acetate, butyl acetate.

Preparing Novel Crystalline Form of Losartan Potassium (Form X)

According to WO 03048135, which generally teaches formation of Form V of losartan potassium from a solvent system comprising one of $C_1$ to $C_6$ alcohols and hexane, we would expect to be able to isolate a polymorph form with strongest diffractions in powder X-ray difractogram at around $2\theta=6.4$, 12.2, 20.7, 21.5 and 22.5°, from a solvent system methanol-hexane.

Surprisingly, we have found that in the case that potassium salt of losartan Form I was dissolved in methanol and the obtained solution was concentrated until thick glass like mass, and the mass was under stirring poured into hexane, and the obtained solid was filtered and dried with caution, a new polymorph form of potassium salt of losartan was formed, characterized by strongest diffractions in powder X-ray difractogram at around $2\theta=6.9$, 13.8, 20.6, 24.0, 24.8, 28.7 and 29.2°, which is one of the embodiments of the invention and for which the name Form X is used. With regard to the mode of isolation the embodiments of the invention are also the solvates of a new polymorph form exhibiting strongest diffractions in powder X-ray difractogram at around $2\theta=6.9$, 13.8, 20.6, 24.0, 24.8, 28.7 and 29.2°.

It is interesting that the new polymorph was formed in a mixture with known Form I if losartan potassium was dissolved in a mixture of methanol and water, and the obtained solution concentrated and poured to diisopropyl ether at room temperature.

Figure 31:
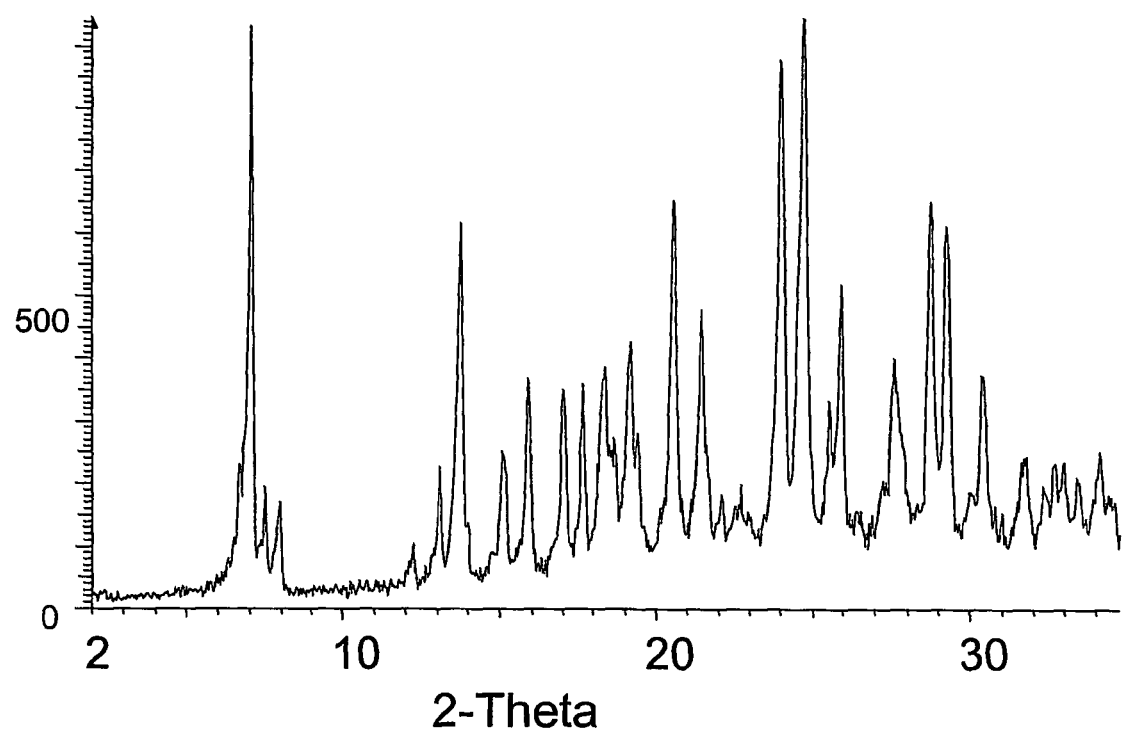
FIG. 31: X-ray powder diffraction pattern of crystalline potassium salt of losartan (Form X)

In an aspect, the present invention, therefore, provides a potassium salt of losartan in crystalline form, characterized by a powder X-ray diffraction pattern with peaks at about $2\theta=6.9$, 13.8, 20.6, 24.0, 24.8, 28.7 and 29.2° (Form X), in another aspect a potassium salt of losartan in crystalline form is provided, characterized by a powder X-ray diffraction pattern essentially as depicted in FIG. 31 and, in yet another aspect, a potassium salt of losartan in crystalline form as described above, characterized in that it is in solvated form.

In yet another aspect, the present invention is a process for preparing potassium salt of losartan in crystalline form as described above (Form X), characterized by isolating from methanol or a mixture of solvent comprising methanol, preferably by isolation from a mixture of methanol and alkane, preferably when alkane is hexane or heptane, more preferably, n-heptane, more preferably, a process characterized by comprising the following steps: preparing a methanolic solution of potassium salt of losartan; concentrating the obtained solution; stirring the obtained concentrated solution with hexane or heptane; and isolating the potassium salt of losartan in crystalline form (Form X).

In yet another aspect, the present invention is an industrial scale process for preparatng potassium salt of losartan in crystalline form exhibiting a powder X-ray diffraction pattern with peaks at about $2\theta=6.9$, 13.8, 20.6, 24.0, 24.8, 28.7 and 29.2° (Form X), characterized by comprising the following steps: removing the protecting group from 2-n-butyl-4-chloro-5-hydroxymethy-1-[2'-triphenylmethyl-2H-tetrazol-5-yl)[1,1'-biphenyl-4-yl]methyl]imidazole; forming a potassium salt with potassium alcoholate; and crystallizing, optionally seeding, with some crystal of crystalline losartan potassium of Form X; isolating and, optionally, milling potassium salt of losartan in crystalline form.

Preparing Novel Crystalline Form of Losartan Potassium (Form Y)

As mentioned, WO 03048135 teaches formation of a Form V from a solvent system comprising one of $C_1$ to $C_6$ alcohols and hexane, From a solvent system $C_1$-hexane, a polymorph Form X can be prepared by dissolving losartan potassium in methanol, concentrating the obtained solution, pouring the obtained concentrated solution into hexane under intensive stirring, the solvents optionally being of industrial grade, or the solution optionally containing a small amount of water, and filtering obtained solid crystalline form.

Present invention provides for forming a new polymorph form of potassium salt of losartan, characterized by strongest diffractions in powder X-ray difractogram at around $2\theta=6.7$, 13.8, 17.4, 19.2, 24.5, 24.8, 25.2 and 28.9°, for which the name Form Y is used. With regard to the mode of isolation, the embodiments of the invention are also the solvates of the new polymorph.

In an embodiment, present invention provides a process for preparing a new polymorph form of potassium salt of losartan, characterized by strongest diffractions in powder X-ray difractogram at around $2\theta=6.7$, 13.8, 17.4, 19.2, 24.5, 24.8, 25.2 and 28.9°, as follows: if potassium salt of losartan is dissolved in methanol to obtain a clear and transparent solution, and this solution is evaporated until resinous or waxy residue, which is nevertheless still transparent and clear and, further, hexane in a few times the surplus of volume with regard to methanol, is added at room temperature, and the mixture is intensively stirred at room temperature, a new polymorph form is obtained following isolation.

The new polymorph as described above is obtained in yet another embodiment of the invention provided a clear and transparent methanolic solution of potassium salt of losartan was under stirring at room temperature added to an alkane in some ten times surplus of volume with regard to methanol, optionally containing a small amount of water, seeded with a few crystals of Form Y, and isolated. With regard to the mode of isolation, the embodiments of the invention are also the solvates of the new polymorph.

Polymorph from Y can be transformed into polymorph form X by drying in vacuo, or at normal pressure at room or higher temperature.

Figure 33:
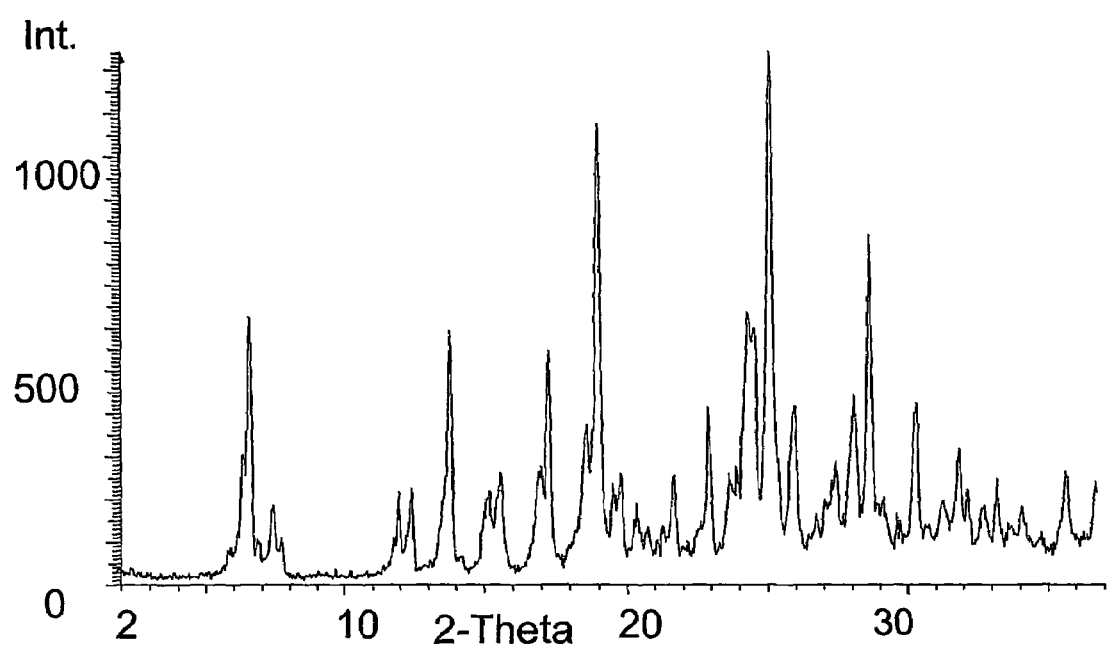
FIG. 33: X-ray powder diffraction pattern of crystalline potassium salt of losartan (Form Y)
Figure 34:
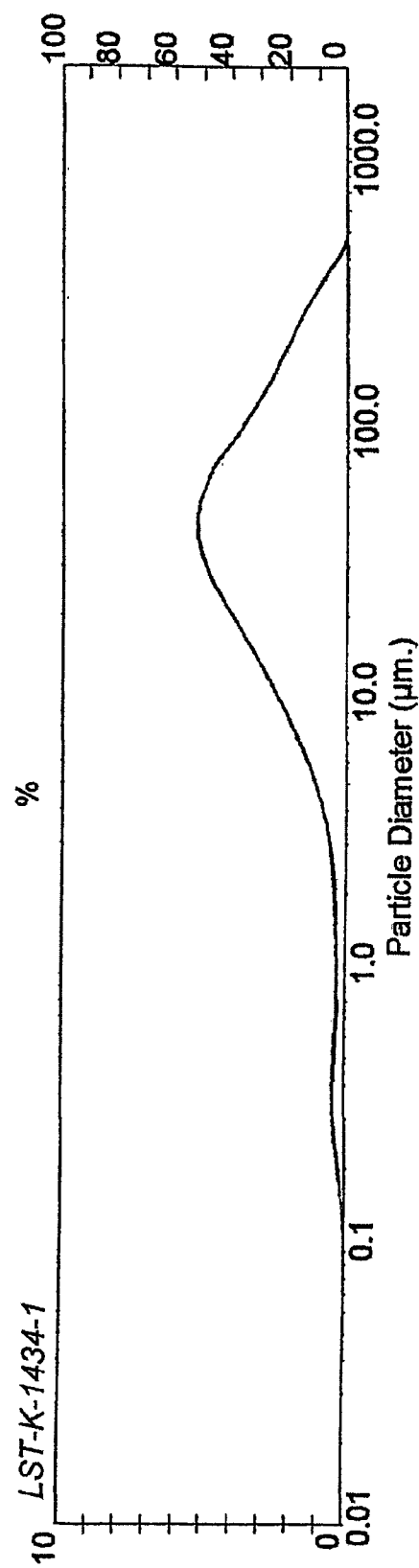
FIG. 34: Particle size distribution of the particles of Batch LST-K-1434/1 of example 47
Figure 35:
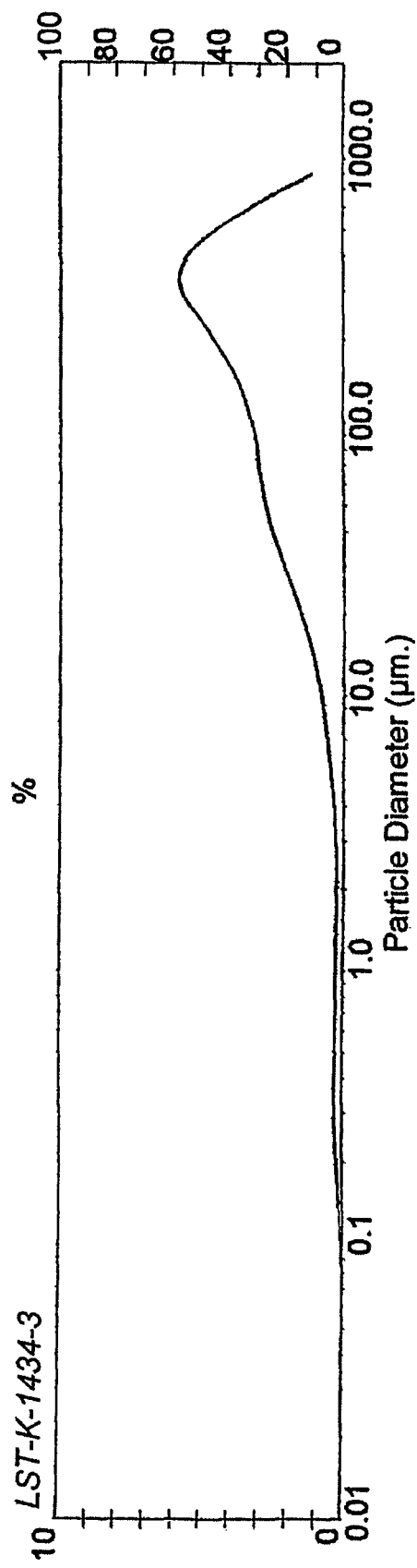
FIG. 35: Particle size distribution of the particles of Batch LST-K-1434/3 of example 47
Figure 36:
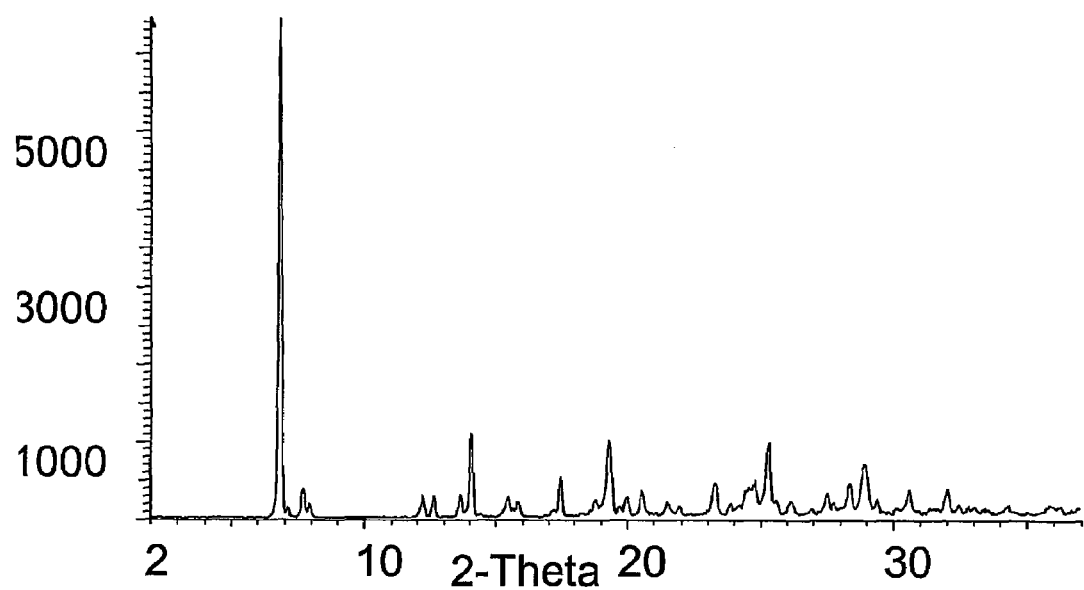
FIG. 36: X-ray powder diffraction pattern of product obtained in Batch L-3391/A

In an aspect, present invention, therefore provides, a potassium salt of losartan in crystalline form, characterized by a powder X-ray diffraction pattern with peaks at about 2θ=6.7, 13.8, 17.4, 19.2, 24.5, 24.8, 25.2 and 28.9° (Form Y), in another aspect providing a potassium salt of losartan in crystalline form, characterized by a powder X-ray diffraction pattern essentially as depicted in FIG. 33 and, in yet another aspect, providing a potassium salt of losartan in crystalline form as described above, characterized in that it is in solvated form.

In yet another aspect, present invention is a process for preparing potassium salt of losartan in crystalline form, characterized by a powder X-ray diffraction pattern with peaks at about 2θ=6.7, 13.8, 17.4, 19.2, 24.5, 24.8, 25.2 and 28.9° (Form Y), or solvates thereof, characterized by isolation from the mixture of methanol and hexane wherein the volume of hexane exceeds the volume of methanol, preferably characterized by comprising the following steps: preparing a clear methanolic solution of potassium salt of losartan; optionally concentrating the obtained solution; mixing the obtained, optionally concentrated, solution with hexane, wherein the volume of hexane exceeds the volume of methanol; and isolating potassium salt of losartan in crystalline form.

In yet another aspect, present invention is a process of converting potassium salt of losartan in crystalline form exhibiting a powder X-ray diffraction pattern with peaks at about 2θ=6.7, 13.8, 17.4, 19.2, 24.5, 24.8, 25.2 and 28.9° (Form Y), or solvates thereof into potassium salt of losartan in crystalline form exhibiting a powder X-ray diffraction pattern with peaks at about 2θ=6.9, 13.8, 20.6, 24.0, 24.8, 28.7 and 29.2° (Form X), characterized by drying in vacuo or at normal pressure, at room temperature or higher temperature.

Pharmaceutical Compositions Containing Novel Salts and Polymorph Forms of Losartan Present invention provides pharmaceutical compositions containing novel salts and polymorph forms of losartan.

An active pharmaceutical ingredient should posses certain desired physical and chemical properties, i.e., solubility in water and certain solvents, adequate particle size, stability, hydroscopic properties, which can be regulated by the choice of a suitable salt, complex and form, which allows reaching effective bio-availability. One of the main criteria is purity which is through purifying and transformation amphoter-alkali or earth-alkali salt-amphoter fulfilled by the novel salts and polymorph forms prepared from losartan purified in accordance with present invention.

In one of the embodiments, present invention provides for a pharmaceutical composition comprising alkali salts or earth-alkali salts of losartan, preferably amorphous alkali salts, or earth-alkali salts of losartan, In another embodiment, present invention provides for a pharmaceutical composition comprising potassium salt of losartan, preferably potassium salt of losartan selected from amorphous salt, or potassium salt of losartan in polymorph form exhibiting strongest diffractions in powder X-ray difractogram at around 2θ=13.0, 17.2, 19.7, 20.9, 21.0, 23.2, 23.6, 24.5, 25.0, 26.6, 17.3, 28.2, 29.0, 31.5°, or potassium salt of losartan in polymorph form exhibiting strongest diffractions in powder X-ray difractogram at around 2θ=6.9, 13.8, 20.6, 24.0, 24.8, 28.7 in 29.2° or potassium salt of losartan in polymorph form exhibiting strongest diffractions in powder X-ray difractogram at around 2θ=6.7, 13.8, 17.4, 19.2, 24.5, 24.8, 25.2 and 28.9°, and solvates thereof.

The pharmaceutical composition can be in a form suitable for peroral or parental application and is, e.g., indicated for treating hypertension. The pharmaceutical composition in accordance with present invention can, e.g., be embodied in the form of tablets, capsules, pellets, granules, and suppositories or their combined forms. Solid pharmaceutical compositions can be shielded, e.g., coated with the aim of increasing peletability or regulating the disintegration or absorption.

In one embodiment of the invention there were prepared film coated tablets by direct compression. Potassium salt of losartan was mixed with lactose, microcrystalline cellulose, starch, and aerosil, and the mixture was sieved. Magnesium stearate was added and mixed again. Cores with a mass of 160 mg were tableted. Cores were coated with a suspension comprising the following essential ingredients: hydroxy propyl methyl cellulose, hydroxy propyl cellulose, polyethylene glycol, and titan dioxide in water or alcohol and the film coated tablets were polished with talc.

Different salts and different polymorph forms require different techniques. The pharmaceutical composition comprising alkali or earth-alkali salts of losartan can be prepared by other suitable procedures, e.g., by dry granulation or peletization. In order to achieve optimum process parameters, particles of an active pharmaceutical ingredient should posses certain desired physical and chemical properties, most importantly appropriate particle size and appropriate bulk and tapped density.

We have discovered that the most suitable particle size of crystalline losartan potassium to be incorporated into pharmaceutical composition using the process of present invention is defined by having more than 90% of the particles with a diameter below 300 μm, more preferably, having particle size parameters: d(0,5)=135 μm and d(0.9)=286 μm.

Apparent volume according to European pharmacopoeia bulk density and tapped density as described in USP 26, <616> of crystalline losartan potassium to be incorporated into pharmaceutical composition were measured. A batch most suitable for pharmaceutical use was identified, and used for further formulation studies.

Pharmaceutical compositions, i.e., a finished dosage form must, when administered by a mammal, exhibit certain bio-availability. A prerequisite for bio-availability is usually that the finished dosage form dissolves when administered so that the body fluids can transport the dissolved active ingredient throughout the body. The dissolution profiles of pharmaceutical compositions according to our invention were measured by the method described in US Pharmacopoeia, using Apparatus 2 at 50 rpm in medium water.

In a preferred embodiment, a solid unit dosage form comprising losartan potassium was prepared by direct compression of a mixture of potassium salt of losartan in polymorph form exhibiting strongest diffractions in powder X-ray difractogram at around 2θ=6.9, 13.8, 20.6, 24.0, 24.8, 28.7 and 29.2°, and pharmaceutically acceptable excipients. The dosage form thus formed was coated as follows: hydroxypropyl cellulose, ethyl cellulose or stearic acid, and triethyl citrate were dissolved under stirring in ethanol, and then homogenized. A suspension of pigments and talc in ethanol was added. The prepared dispersion was sprayed onto cores so that a film coating was obtained. Tablets were polished with talc.

One aspect of the invention, therefore, represents a pharmaceutically active ingredient ready to be incorporated into a pharmaceutical formulation, which is a potassium salt of losartan in crystalline form, chosen from the one exhibiting a powder X-ray diffraction pattern with peaks at about 2θ=6.7, 13.8, 17.4, 19.2, 24.5, 24.8, 25.2 and 28.9°; the one exhibiting a powder X-ray diffraction pattern with peaks at about 2θ=6.9, 13.8, 20.6, 24.0, 24.8, 28.7 and 29.2°, and the one exhibiting a powder X-ray diffraction pattern with peaks at about 2θ=13.0, 17.2, 19.7, 20.9, 21.0, 23.2, 23.6, 24.5, 25.0, 26.6, 17.3, 28.2, 29.0, 31.5°, characterized in that it comprises more than 50% of particles having a diameter between around 5 μm and around 500 μm.

Another aspect of the invention represents a pharmaceutically active ingredient ready to be incorporated into a pharmaceutical formulation, which is amorphous potassium salt of losartan, characterized in that it comprises more than 50% of particles having a diameter between around 5 μm and around 500 μm.

Yet another aspect of the invention represents a pharmaceutically active ingredient ready to be incorporated into a pharmaceutical formulation, which is potassium salt of losartan as described above, characterized by comprising at least 50% of particles having a diameter below 100 μm.

An aspect of the invention is also use of sodium salt of losartan as medicament, preferably use of sodium salt of losartan for manufacturing a medicament for the treatment of hypertension.

Another aspect of the invention is also use of potassium salt of losartan in crystalline form with bound water, characterized by a powder X-ray diffraction pattern with peaks at about 2θ=13.0, 17.2, 19.7, 20.9, 21.0, 23.2, 23.6, 24.5, 25.0, 26.6, 17.3, 28.2, 29.0, 31.5° wherein the water content is between around 7% and 12% by weight, or use of potassium salt of losartan in crystalline form, characterized by a powder X-ray diffraction pattern with peaks at about 2θ=6.9, 13.8, 20.6, 24.0, 24.8, 28.7 29.2° (Form X), or solvates thereof, or use of potassium salt of losartan in crystalline form, characterized by a powder X-ray diffraction pattern with peaks at about 2θ=6.7, 13.8, 17.4, 19.2, 24.5, 24.8, 25.2 and 28.9° (Form Y), or solvates thereof, as a medicament.

Yet another aspect of the invention is use of crystalline potassium salt of losartan for manufacturing a medicament for the treatment of hypertension wherein the crystalline potassium salt of losartan is selected from the one exhibiting a powder X-ray diffraction pattern with peaks at about 2θ=6.9, 13.8, 20.6, 24.0, 24.8, 28.7 and 29.2°, the one exhibiting a powder X-ray diffraction pattern with peaks at about 2θ=6.7, 13.8, 17.4, 19.2, 24.5, 24.8, 25.2 and 28.9°, or solvates thereof, or one with bound water exhibiting a powder X-ray diffraction pattern with peaks at about 2θ=13.0, 17.2, 19.7, 20.9, 21.0, 23.2, 23.6, 24.5, 25.0, 26.6, 17.3, 28.2, 29.0, 31.5° wherein the water content is between around 7% and 12% by weight, Embodiments of the invention are also a pharmaceutical composition comprising sodium salt of losartan as an active ingredient and pharmaceutically acceptable excipients, and a pharmaceutical composition comprising an earth-alkali salt of losartan as an active ingredient and pharmaceutically acceptable excipients, and a pharmaceutical composition comprising potassium salt of losartan in crystalline form with bound water, characterized by a powder X-ray diffraction pattern with peaks at about 2θ=13.0, 17.2, 19.7, 20.9, 21.0, 23.2, 23.6, 24.5, 25.0, 26.6, 17.3, 28.2, 29.0, 31.5° wherein the water content is between around 7% and 12% by weight as an active ingredient, and pharmaceutically acceptable excipients and a pharmaceutical composition comprising potassium salt of losartan in crystalline form characterized by a powder X-ray diffraction pattern with peaks at about 2θ=6.9, 13.8, 20.6, 24.0, 24.8, 28.7 and 29.2° (Form X), or solvates thereof, and a pharmaceutical composition comprising potassium salt of losartan in crystalline form, characterized by a powder X-ray diffraction pattern with peaks at about 2θ=6.7, 13.8, 17.4, 19.2, 24.5, 24.8, 25.2 and 28.9° (Form Y) or solvates thereof.

One of the embodiments is a pharmaceutical composition comprising potassium salt of losartan in crystalline form sensitive to moisture, comprising from about 25% to 33% potassium salt of losartan; from 55% to 70% by weight of microcrystalline cellulose; from 2% to 10% by weight croscarmellose; and anhydrous silica, preferably characterized in that it is coated, and that the coating comprises from around 25% to around 70% of hydroxypropylcellulose, from around 5% to around 15% alkyl citrate and, optionally comprises from around 10% to 45% stearic acid or ethylcellulose by weight of the total weight of the coating.

Potassium salt of losartan incorporated into described pharmaceutical compositions can be combined with other pharmaceutical active ingredients, i.e. a diuretic.

EXPERIMENTAL PART

Techniques

Prepared novel salts of losartan and novel polymorph forms were characterized by the following physical and chemical methods:
  determination of melting point
  differential scanning calorimetry
  NMR spectroscopy
  IR spectroscopy
  powder X-ray diffraction spectroscopy
  thermogravimetry
  dynamic vapour sorption
  measurement of the particle size, and specific area of the particles
  measurement of the bulk and tapped density The results were compared to known literature data, or to the characteristics of the known crystalline potassium salt of losartan prepared according to the teaching of U.S. Pat. No. 5,608,075.

Crystalline potassium salt prepared by the procedure of transformation amphoter-potassium salt-amphoter was recognized as known Form I, and was identical to the one prepared following the teaching of U.S. Pat. No. 5,608,075. Sodium, magnesium and calcium salt, which were not known before, were also characterized. Calcium and magnesium salts were prepared as amorphous substances. Sodium salt was prepared as amorphous and crystalline substance. Losartan potassium was prepared as amorphous solid as well as three distinct polymorph forms, which were all characterized.

Melting Point Determination

The melting point was determined by a visual method using a microscope with heated table (Kofler microscope), or method according to Thiele.

The measured melting point of amorphous losartan potassium does not differ substantially from the melting point of crystalline losartan potassium, Samples melt between 265° C. and 275° C., the visual processes are more continuous at amorphous substance with regard to the coloring and flowing of the sample, while at crystalline Form I, a change can be determined at around 230° C., which is a temperature known from literature as conversion into Form II.

The differences between melting points of crystalline and amorphous sodium salt of losartan differ. Crystalline melts at 191-196° C., while amorphous liquefies at 171-177° C. We did not detect melting of calcium or magnesium salt below 300° C.

Differential Scanning Calorimetry

Analyses were performed on differential dynamic calorimeter Perkin Elmer Pyris 1 DSC.

Crystalline losartan potassium Form I exhibits a first endothermic signal above 230° C., which is accordance with known transition to Form II. Amorphous potassium salt does not exhibit this signal, though substantial changes occur at lower temperature wherein an extensive exotermic signal can be seen between 190° C. and 210° C. Above this temperature the samples decompose completely, and are visually changed.

Crystalline sodium salt of losartan exhibits a melting point as determined by DSC at 195° C. which complies with melting point determination as described above. Substantial endotherm was detected already in the range around 110° C., which hints to the possible loss of bound water. Amorphous sodium salt of losartan does not exhibit this change; transformations above 240° are marked by decomposition of samples. Above 150° C. there is barely visible a very broadened transition, which corresponds to the observations on Kofler microscope.

DSC thermograms of samples of magnesium and calcium salts of losartan are similar to thermograms of amorphous sodium salt of losartan, decomposition of samples is visible with somewhat different dynamics of heat flows.

DSC thermogram of a potassium salt of losartan of form with bound water, exhibiting a powder X-ray diffraction pattern with peaks at about 2θ=13.0, 17.2, 19.7, 20.9, 21.0, 23.2, 23.6, 24.5, 25.0, 26.6, 17.3, 28.2, 29.0, 31.5° wherein the water content is between around 7% and 12% by weight, shows a broadened peak until 75° C. which indicates the loss of first molecule of water, at around 90° C. there is a second sharp endothermic signal, which is probably a simultaneous loss of other two waters, and demolishing of an orderly structure into an amorphous one. An amorphous form has a higher level of entropy than a crystalline form, therefore the transition is an endothermic process. At 190-200° C. the amorphous substance crystallizes again.

Figure 32:
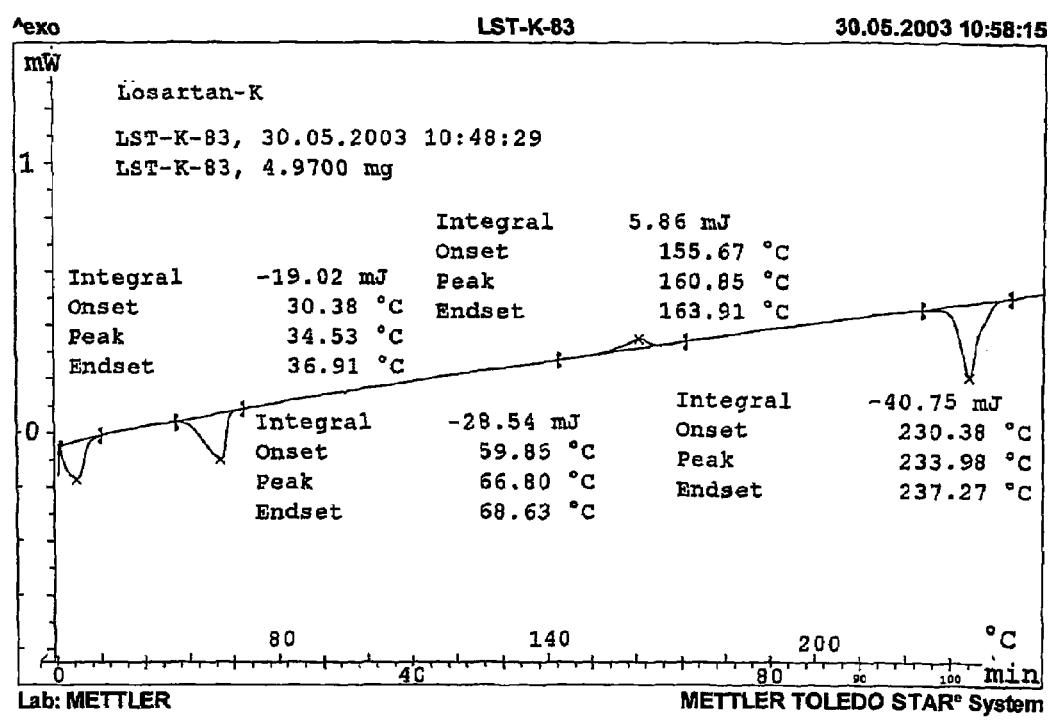
FIG. 32: DSC thermogram of crystalline potassium salt of losartan obtained by process of example 44

DSC thermogram of a sample isolated in the process described in the Example 44 is depicted in FIG. 32.

$^{13}$C CP/MAS NMR Solid State Spectroscopy

Varian instrument INOVA 600 at 150 kHz was used. Samples were measured with TOSS at spinning 10 kHZ, pulse (90) 4.4μ.

The solid state nuclear magnetic resonance spectroscopy is a suitable method for determining the structure of solid samples. Thus, individual polymorphic modification can be determined. In an easy manner, solvates or conformational polymorphs can be determined. High resolution spectra and signals with good intensities can be obtained with CP/MAS (cross-polarization/magic angle spinning spectrum) technique [Sedon K. R. et al. Crystal Engineering: The Design and Application of Functional Solids, Kluwer Academic Publishers, 1999]. Measuring different polymorphs $^{13}$C NMR we would expect identical spectra due to identical bonding of carbon atoms, a difference is shown, however, on the basis of the chemical environment in respective substances [Bugay D. E.: Magnetic Resonance Spectrometry v: Brittain H. G. Physical Characterization of Pharmaceutical Solids]. It is most easy to determine the structure of samples, which are pure and contain one crystalline form only. In the case of mixtures we observe chemical shifts which can overlap and mislead the interpretation. Spectra of amorphous solids are usually simpler due to the absence of certain information, which in crystalline structure were a function of a specific environment of respective nuclei. This environment is not repeatable in an amorphous solid.

Spectra of two forms of losartan potassium have been recorded. Crystalline Form I exhibits sharp peaks, while amorphous form has broader signals whereby some signals are melted with neighboring peaks, or are absent. Spectra are shown in the Figures, and characteristic signals are listed in Table 2.

TABLE 2

$^{13}$C Chemical shifts of solid samples of losartan potassium recorded by NMR CP/MAS

| Form I (ppm) | amorphous (ppm) |
|---|---|
| 14.1 | 13.8 |
| 17.1 | / |
| 21.0 | 22.3 |
| 27.8 | 26.8 |
| 30.4 | 29.0 |
| / | 47.1 (broad) |
| 50.0 (broad) | 52.0 (broad) |
| 123.8 | / |
| 126.5 | 127.4 |
| 130.3 | 129.2 |
| 131.7 | overlapped |
| 134.6 | / |
| 136.1 | 135.6 |
| 141.7 | 140.9 |
| 146.6 | / |
| 148.1 | 148.7 |
| 163.0 | 162.4 |

IR Spectroscopy

IR spectrometer Bio-Rad FTS-60, Digilab-Division was used.

Infrared spectroscopy is a method, which detects low energy transition, especially at the levels of bonds, which are the consequence of molecular vibrations and oscillations. They mainly depend on the nature of the bond, but also on the neighbourhood of the molecule, IR spectroscopy is, therefore, a widely accepted technique for studies of polymorphs. It is, though, not necessary that different crystalline forms will exhibit different IR spectra, differences can be subtle.

The characteristic peaks of recorded IR spectra of various salts of losartan and forms thereof are listed in Table 3 as measured or from literature.

TABLE 3 characteristic signals [cm$^{-1}$] in IR spectra of salts of losartan in a range between 1550-700 cm$^{-1}$

| K salt (Form I) | K salt (Form II) | amorph. K salt | crystalline Na salt | amorph. Na salt | Mg salt | Ca salt |
|---|---|---|---|---|---|---|
| 1507 | | 1506 | 1507 | 1507 | 1507 | 1508 |
| 1497 | | 1495 | 1498 | 1494 | 1495 | 1494 |
| 1472 | | / | 1474 | / | / | / |
| 1460 | | 1459 | 1461 | 1460 | 1461 | 1461 |
| 1423 | | 1424 | 1426 | 1425 | 1426 | 1426 |
| 1406 | | 1408 | 1408 | 1408 | 1409 | 1409 |
| 1378 | | 1380 | weak | 1380 | 1380 | 1380 |
| 1358 | 1357 | 1356 | 1360 | 1358 | 1359 | 1358 |
| 1342 | | / | 1342 | / | / | / |
| 1260 | | 1255 | 1264 | 1256 | 1258 | 1258 |
| / | | 1144 | 1140 | 1144 | 1150 | 1148 |
| 1133 | | 1126 | 1132 | overlap | overlap | overlap |
| 1113 | | 1107 | 1109 | 1108 | 1108 | 1108 |

TABLE 3-continued characteristic signals [cm$^{-1}$] in IR spectra of salts of losartan in a range between 1550-700 cm$^{-1}$

| K salt (Form I) | K salt (Form II) | amorph. K salt | crystalline Na salt | amorph. Na salt | Mg salt | Ca salt |
|---|---|---|---|---|---|---|
| 1074 | | 1073 | 1080 | 1074 | 1075 | 1075 |
| / | | 1011 | 1011 | 1013 | 1014 | 1014 |
| 1008 | | 1005 | 1008 | 1006 | 1006 | 1006 |
| 996 | | / | / | / | / | / |
| 954 | / | 954 | 958 | 954 | 953 | 954 |
| / | | / | 949 | / | / | / |
| 934 | 940 | 933 | 937 | 933 | 934 | 934 |
| 886 | / | 879 | / | weak | weak | 878 |
| 844 | | / | / | / | / | / |
| 841 | | / | 839 | / | / | / |
| 826 | | 825 | 820 | 824 | 824 | 824 |
| 789 | | 786 | 785 | 787 | 787 | 786 |
| 763 | 754 | 760 | 753 | 761 | 760 | 760 |
| melted with 63 | | 742 | 740 | 743 | melted with 760 | 743 |
| 713 | / | 715 | weak | weak | 714 | 714 |

IR spectra of amorphous and crystalline potassium salt differ substantially throughout the entire scale, above all in the form of absorption peaks and minor shifts of absorption maximums. Characteristic for amorphous losartan potassium is the absence of peaks at 1472±5, 1342±5 and between 835 in 845 cm$^{-1}$ as compared to Form I, and the presence of peaks 954±5, 949±5, 870-890, and 715±5 cm$^{-1}$, as compared to Form II.

The IR spectrum of crystalline sodium salt of losartan is more similar to Form I of losartan potassium than to amorphous sodium salt, but differs by the absence of peaks 995-1000 and 870-890 cm$^{-1}$ and 820-850 cm$^{-1}$, with peaks at 839±1 in 820±1 cm$^{-1}$. Amorphous sodium salt differentiate from crystalline form by the absence of peaks in ranges 1472±5, 1342±5 and 835-845 cm$^{-1}$.

All amorphous salts have very similar IR spectra, which can possibly be attributed to the fact that there is no specific absorption caused by the effect of cation on energetic levels of respective bonds. The effects on the inter-molecular scale are due to the amorphous state diffused and not detectable in IR spectra.

Powder X-Ray Diffraction Spectroscopy

Samples were recorded on Philips PW1710 with reflexion technique: CuKα radiation, range from 2° to 37°2θ, step 0.040° 2θ, integration time 1 sec.

The X-ray diffraction spectroscopy is much more precise than IR or solid state NMR spectroscopic methods for determining polymorph forms. While the latter only provide information on atoms and bonds which directly interact with neighboring molecules, a crystal lattice can be defined with X-ray diffraction, From an X-ray diffraction pattern of an orderly monocrystal there can be precisely defined the special image of a molecule. From an X-ray diffraction pattern of a powdery substance there can be established differences among different crystal lattices, however, there cannot be established the positions of respective atoms. Besides the information on different ordering of the molecules into a crystal, which indicates different crystalline forms, X-ray diffraction spectra provide information on the level of order, i.e., crystallinity, where lower crystallinity causes peaks to broaden. The ultimate form of non-orderness of a solid is amorphous state, which does not show the repeatability of molecular directions and positions in a solid. Completely amorphous substance thus shows diffuse dispersion of a roentgen radiation, which exhibits a continuum of diffractions throughout the whole of the measured range. X-ray powder diffraction spectroscopy is, therefore, a key method for differentiation of crystalline forms and distinguishing crystalline forms from amorphous forms also in cases when other methods do not differentiate among samples.

X-ray diffraction patterns of amorphous alkali and earth-alkali salts of losartan have absent discrete diffraction characteristics for crystalline forms and continuum of diffractions in the entire measured range, which is an indication of amorphous nature of the samples.

X-ray diffraction patterns of samples of potassium salt of losartan in crystalline form with bound water (Form III) exhibit characteristic peaks at about 2θ=13.0, 17.2, 19.7, 20.9, 21.0, 23.2, 23.6, 24.5, 25.0, 26.6, 17.3, 28.2, 29.0, 31.5° independently of the mode of preparation thereof.

Figure 30:
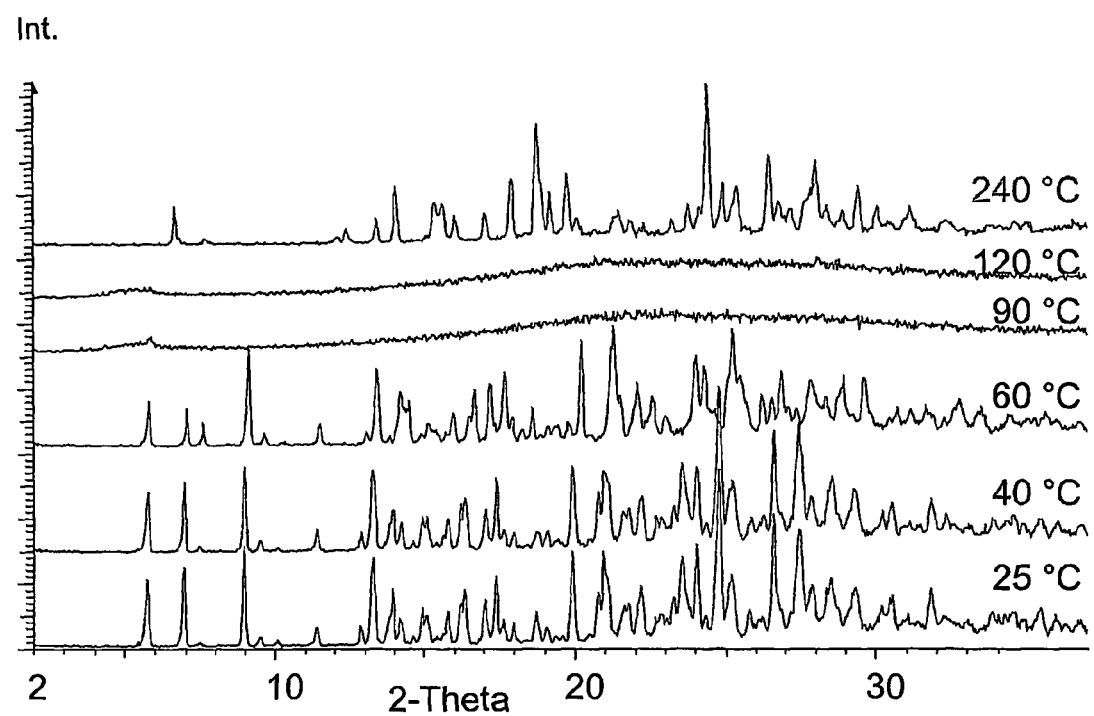
FIG. 30: X-ray powder diffraction patterns of crystalline potassium salt of losartan (crystalline form with bound water) recorded at different temperatures

We have researched the dependence of such X-ray diffraction patterns on the temperature on Siemens D5000 apparatus with reflexion technique at different temperatures (conditions: CuK radiation, range from 2° to 37° 2θ step 0.04° 2θ, integration time 4 sec) Rate of heating was 10° C./min. each measurement took 59 minutes, overall measurement time was 7 h 22 min. Results of measurements are depicted in FIG. 30, X-ray diffraction pattern of samples of potassium salt of losartan in crystalline form (Form X) exhibit characteristic peaks at about 2θ=6.9, 13.8, 20.6, 24.0, 24.8, 28.7 and 29.2°, the sample of potassium salt of losartan in crystalline form (Form Y) exhibits characteristic peaks at about 2θ=6.7, 13.8, 17.4, 19.2, 24.5, 24.8, 25.2 and 28.9°, both X-ray diffractions spectra are presented in FIG. 31 and FIG. 33.

Thermogravimetry (TG)

Figure 26:
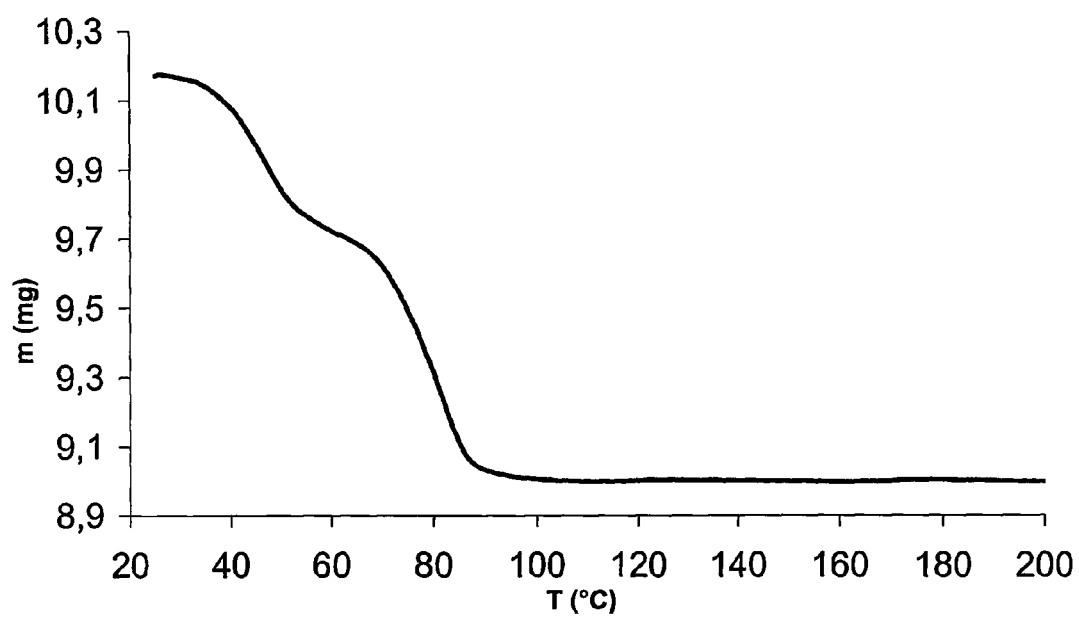
FIG. 26: Thermogram (loss of mass) of crystalline potassium salt of losartan (crystalline form with bound water)

An analysis was performed on Mettler Toledo TGA/SDTA 851e apparatus in 150 mL Pt cups with a diameter of 7 mm in dynamic atmosphere with air flow 100 ml/min. (Heating 5° C./min from 25° C. to 240° C.). FIG. 26 shows the loss of mass with subtracted base line by heating a sample of 10.17 mg of potassium salt of losartan in crystalline form with bound water.

Dynamic Vapour Sorption (DVS)

Measurements were performed on instrument DVS—The Sorption Solution, Surface Measurement Systems Ltd. UK.

The principle of measurement is as follows: The sample measured is placed on one side of a very precise scale, a reference non-hydroscopic sample having been placed on the other side. The scale is located in an isolated chamber in which the relative humidity can be set. The hydroscopic sample being measured binds moisture from the environment, and an increase of mass is detected.

The relative humidity means an amount of moisture in the atmosphere, i.e., ratio between partial pressure of water in the atmosphere and vapour pressure of water at given temperature. Vapour pressure of water is the maximum partial pressure which water can reach at a given temperature. At this temperature the relative humidity is 100%.

The higher the relative humidity, the more water can be absorbed by a hydroscopic measure sample. An equilibrium is established between bound water in a sample and gaseous water in the atmosphere. If relative humidity of the atmosphere is increased, a hydroscopic substance absorbs water again, and a new equilibrium is established. On DVS these equilibriums are seen as a dependence of the sample mass upon the relative humidity of the atmosphere.

Water in a sample can bind as freely bound water, or to specific spaces in crystal lattice as crystally bound water. Crystally bound water is usually in a stechiometric ratio to the molecule, It is bound more strongly than freely absorbed water, and is at heating usually lost simultaneously in a stechiometric amount.

With different salts and their concentrations in a solution there can be established different relative humidity in a closed space, i.e exicator. In an experiment of moistening an atmosphere of 80% relative humidity was used, wherein the pressure of water at 25° C. was 2.46 kPa.

Figure 27:
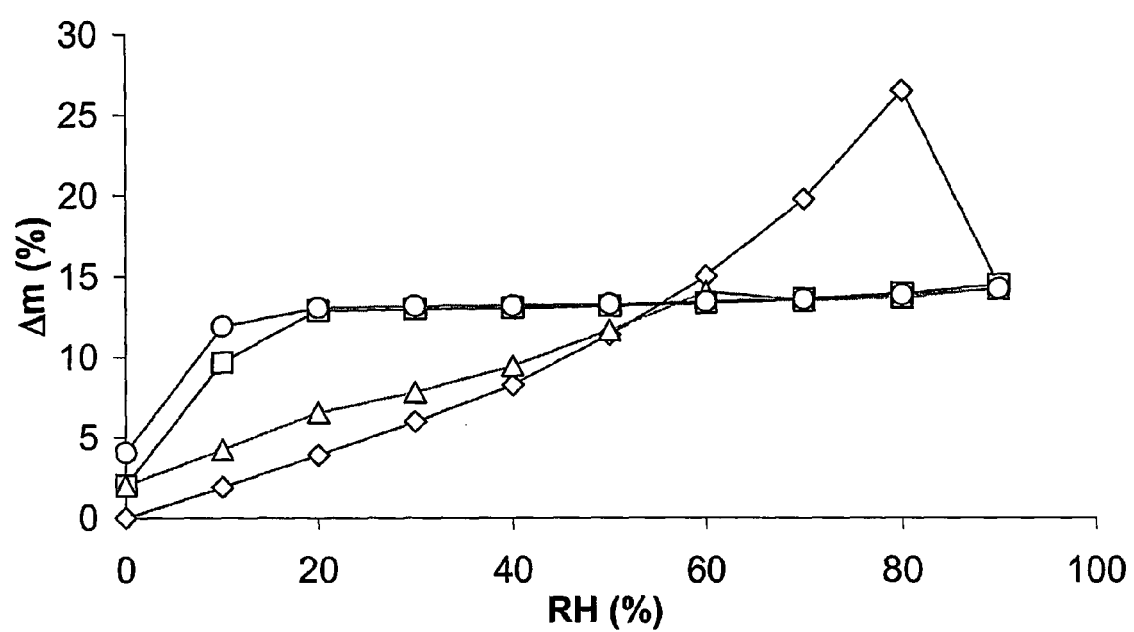
FIG. 27: DVS diagram of crystalline potassium salt of losartan (crystalline form with bound water)
Figure 28:
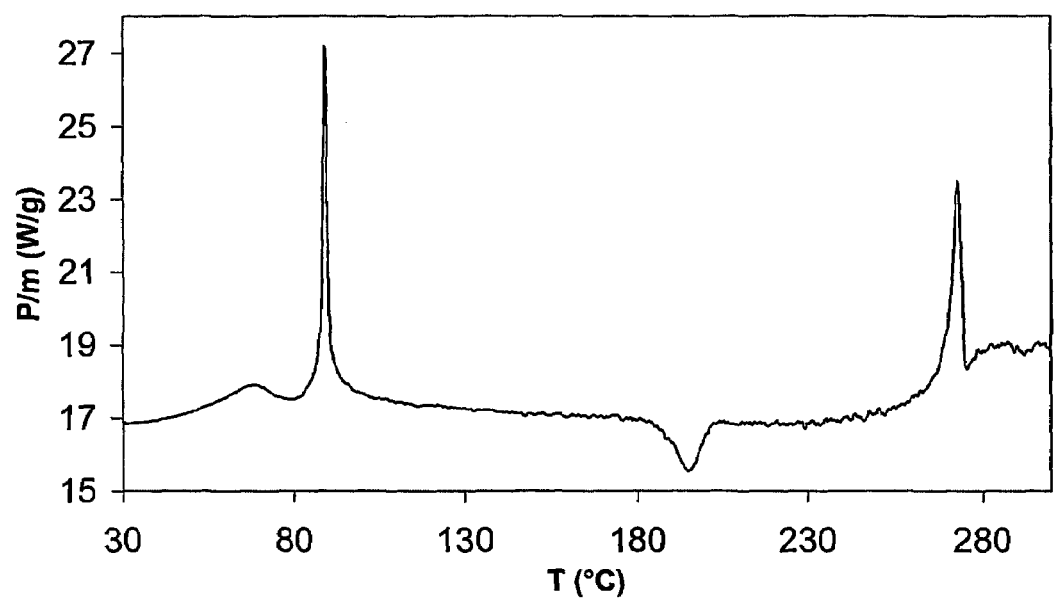
FIG. 28: DSC thermogram of crystalline potassium salt of losartan (crystalline form with bound water)
Figure 29:
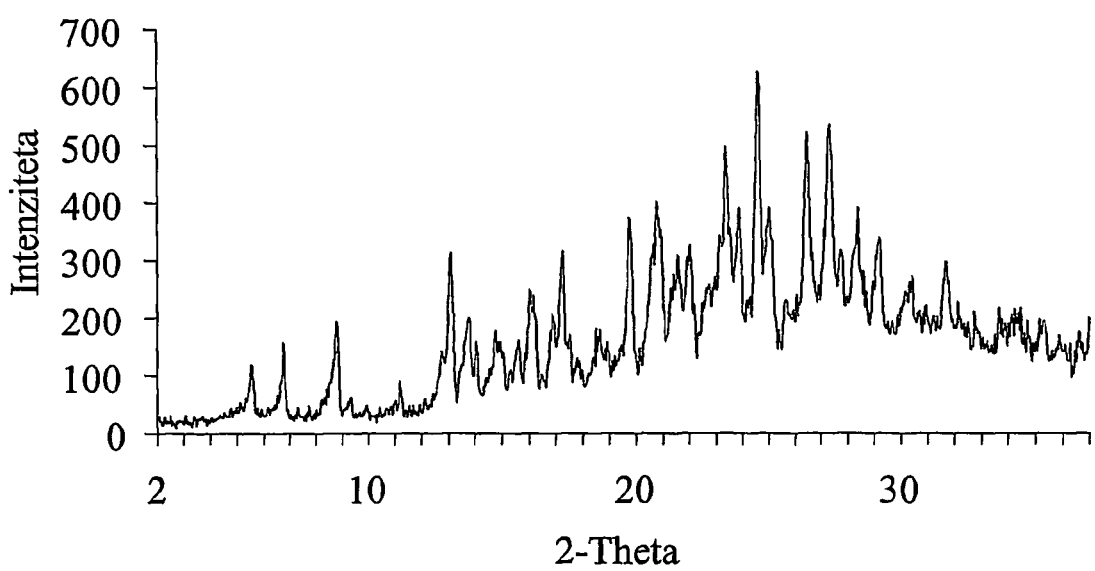
FIG. 29: X-ray powder diffraction pattern of crystalline potassium salt of losartan (crystalline form with bound water)

DVS experiment is shown in FIG. 27. The ordinate axis represents the change of mass, abscise representing the humidity. Line (◇) is the increase of mass of amorphous losartan potassium, which represents the absorption of water until 25% at 80% relative humidity, whereupon crystalline form with bound water crystallizes, which is seen as a drop of mass (content of water in sample is approximately 13%); (□) is a change of mass of formed crystalline form with bound water, while decreasing relative humidity, at relative humidity below 20% the sample loses bound water, and transforms into amorphous form; (Δ) is repeated sorption of water of preceding sample until approximately 13% water content at 60% relative humidity, at which point the amorphous sample crystallizes (○) is a change of mass of previous sample, while decreasing relative humidity. Results prove the repeatability of crystallization from amorphous substance while increasing relative humidity, as well as repeatability of transformation into amorphous substance.

Measurement of the Particle Size, and Specific Area of Particles

The particle size of samples was measured by Malvern Mastersizer S instrument, Sample and 100 mg of DSSS (Dioctyl sulfosuccinate sodium salt) was added to hexane, and the suspension was stirred at 2500 rpm. The distribution of sizes of particles in the sample were determined by scattering of monochromatic light using the theory by Mieje. The results of measurements of representative samples of amorphous substance (Batches LST-K-1434/1, LST-K-1434/2, LST-K-1434/3) are shown in Table 4. Table 5 lists the particle sizes and solubility parameters of samples of substance crystallized in various crystalline forms, and milled to different sizes.

TABLE 4

Size of the particles and specific area of amorphous losartan potassium

| | | LST-K-1434/1 | LST-K-1434/2 | LST-K-1434/3 |
|---|---|---|---|---|
| PARTICLE SIZE | d 0.1 (μm) | 5.2 | 5.6 | 10 |
| | d 0.5 (μm) | 36 | 63 | 144 |
| | d 0.9 (μm) | 152 | 322 | 484 |
| | D[4.3] | 61 | 120 | 202 |
| | Estimated specific area (m²/g) | 1.1 | 1.1 | 1.0 |
| SPECIFIC AREA | BET isotherm calculated surface area (m²/g) | 1.27 | 0.77 | 0.48 |

TABLE 5

Size of the particles and solubility parameters of crystalline forms of losartan potassium

| | | LST-K-1481 | LST-K-1496/1 | Form I | Milled sample of Form I |
|---|---|---|---|---|---|
| PARTICLE SIZE | d 0.1 (μm) | 8.3 | 1.1 | 20 | 3.3 |
| | d 0.5 (μm) | 96 | 25 | 86 | 34 |
| | d 0.9 (μm) | 215 | 58 | 218 | 86 |
| | D[4.3] | 107 | 28 | 105 | 41 |
| SOLUBILITY (mg/ml) | in water | 633 | | 630 | |
| | in 0.1 M HCl | 1.74 | | 1.52 | |
| | in glycerole | 2.83 | | | |
| RATE OF DISSOLUTION (min) | 75 mg in 50 ml 0.1 M HCl | 14 | 13 | 16 | 8 |

Measurement of the Bulk and Tapped Density

Bulk and tapped density were measured in accordance with PhEur4, 2.9.15 and USP 26, <616> and are shown in Table 6.

TABLE 6

Bulk and tapped density and volume of samples of losartan potassium

| | LST-K-1434/1 | LST-K-1434/2 | LST-K-1434/3 |
|---|---|---|---|
| bulk density (g/ml) | 0.21 | 0.32 | 0.43 |
| tapped density (g/ml) | 0.27 | 0.41 | 0.52 |
| bulk volume (ml/g) | 4.69 | 3.16 | 2.32 |
| tapped volume (ml/g) | 3.70 | 2.45 | 1.91 |
| Carr index | 21.0 | 22.6 | 17.8 |
| Hausner index | 1.27 | 1.29 | 1.22 |

The following Examples further illustrate the invention. They are provided for illustrative purposes only, and are not intended to limit the invention in any way.

EXAMPLE 1

Crude Losartan (2-n-butyl-4-chloro-5-hydroxymethyl-1-[[2'-(1H-tetrazole-5-yl)-biphenyl-4-yl]metyl]-1H-imidazole)

A mixture of 29.80 g 5-[2-(4-bropmomethylbiphenyl)]-2-triphenylmethyl-2H-tetrazole, 43.4 g 2-n-butyl-4-chloro-5-hydroxymethyl-1H-imidazole and 38.27 g potassium carbonate n 550 ml N,N-dimethylacetamide was stirred at a temperature of 0-5° C. for 8 hours and at room temperature overnight, To the mixture 8.02 g $NaBH_4$ and 18 ml water were added. The reaction mixture was cooled to room temperature and intensively stirred for 3 hours. The reaction mixture was under intensive stirring poured into 1.1 l water, filtered, and the precipitate rinsed with 550 ml water. The product was dried in vacuo overnight at room temperature over silica gel.

The obtained 2-n-butyl-4-chloro-5-hydroxymethyl-1-[[2'-(tripheniymethyl-2H-tetrazole-5-yl)][1.1'biphenyl-4-yl]methyl]imidazole was crystallized from chlorobutane and ethyl acetate with final overall yield of 66.77 g after drying.

To a solution of 67.77 g 2-n-butyl-4-chloro-5-hydroxymethyl-1-[[2'-(tripheniymethyl-2H-tetrazole-5-yl)[1.1'biphenyl-4-yl]methyl]imidazole in 316 ml of THF were added under intensive stirring of 105.9 g 12% HCl at a temperature of 23° C. during one hour. The mixture was intensively stirred at room temperature overnight. 30% NaOH solution was added at a temperature of 22° C. during one hour until a pH of 12.5 was reached (approximately 100 ml). THF was evaporated at temperature up to 60° C. and demineralized water was added till starting volume. The precipitate was filtered, rinsed with 2×50 ml demineralized water and disposed. The aqueous phase was extracted with 1×50 ml toluene. The organic solvent phase was separated, and 124 ml ethyl acetate were added to the aqueous phase. The reaction mixture was acidified during intensive stirring with a concentrated $H_2SO_4$ at a temperature of 21-25° C. until a pH of 3.6-3.8. The mixture was cooled below 10° C. and mixed for 1 hour. The precipitate was filtered, digested with 130 ml ethyl acetate, filtered once again and dried overnight in vacuo at a temperature of 50° C. The yield was 40.8 g losartan.

EXAMPLE 2

(Formation of Sodium Salt of Losartan—Method 1)

To 40.81 g losartan of Example 1 in 235 ml i-propanol, a solution of 5.5 g sodium hydroxide in 5.7 ml of water was added at a temperature of 38-40° C. to a pH 12 over half an hour. Approximately 35 ml of azeotropic mixture i-propanol/water were removed by distillation. 140 ml n-heptane were added, and reaction mixture was stirred at room temperature until a white solid has been formed. The resulting susoension was diluted with 55 ml of n-heptane, filtered, washed with 110 ml n-heptane, and dried in vacuo at 50° C. to yield 35.0 g sodium salt of losartan.

Melting point: 191-196° C.

Water according to Karl-Fisher: 4.2%.

Assay of sodium: 4.4% (5.0% calculated to anhydrous substance)

EXAMPLE 3

(Formation of Sodium Salt of Losartan—Method 2)

To 40.81 g losartan of Example 1 in 235 ml i-propanol, a solution of 5.5 g sodium hydroxide in 5.7 ml of water was added at a temperature of 38-40° C. to a pH 10-12 over half an hour. Approximately 35 ml of azeotropic mixture i-propanol/water were removed by distillation, 140 ml of n-heptane were added, and reaction mixture was stirred at room temperature until a white solid was formed. The resulting dispersion was diluted with 55 ml n-heptane, filtered, washed with 110 ml n-heptane, and dried in vacuo at 50° C. to yield 37.0 g sodium salt of losartan.

Melting point: 190-198° C.

Water according to Karl-Fisher: 0.3%.

EXAMPLE 4

(Formation of Sodium Salt of Losartan—Method 3)

To 40.81 g losartan of Example 1 in 120 ml i-propanol, 9.28 g sodium t-butoxide were added. The reaction mixture was clarified, 145 ml n-heptane were added, and it was stirred at room temperature until a white solid was formed. The resulting solid was filtered and washed with 165 ml n-heptane, dried at 40° C. in vacuo to yield 37.0 g of sodium salt of losartan.

Melting point: 191-196° C.

Assay of sodium: 4.7% (5.2% calculated to the anhydrous substance).

EXAMPLE 5

(Formation of Potassium Salt of Losartan—Method 1)

To 40.81 g losartan of Example 1 in 235 ml i-propanol, a solution of 5.5 g potassium hydroxide in 5.7 ml of water was added at a temperature of 38-40° C. to a pH 12 during half an hour. Approximately 35 ml of azeotropic mixture i-propanol/water were removed by distillation, 141.5 ml of n-heptane were added, and reaction mixture was stirred at room temperature until a white precipitate was formed. The resulting precipitate was diluted with 54 ml n-heptane, filtered, washed with 108 ml n-heptane, and dried in vacuo at 50° C. to yield 21.36 g of losartan potassium.

EXAMPLE 6

(Formation of Potassium Salt of Losartan—Method 2)

To 10.2 g losartan of Example 1 in 59 ml i-propanol, a solution of 1.4 g of potassium hydroxide in 1.5 ml of water was added at a temperature of 38-40° C. to a pH of 10 during half an hour. Approximately 19 ml of azeotropic mixture i-propanol/water were removed by distillation, 36 ml n-heptane were added, and reaction mixture was stirred at room temperature until a white solid was formed. The resulting solid was diluted with 14 ml n-heptane, filtered, washed with 26 ml n-heptane, and dried in vacuo at 50° C. to yield 8.57 g losartan potassium.

EXAMPLE 7

(Formation of Potassium Salt of Losartan—Method 3)

To 40.81 g losartan of Example 1 in 110 ml i-propanol was added 10.86 g of potassium t-butanolate a temperature between 10° C. and 25° C. The reaction mixture clarified. A dense white precipitate was formed when 150 ml of n-heptane was added and stirred at room temperature for 1 hour. It was filtered and washed with 75 ml n-heptane, dried at 50° C. C in vacuo overnight to yield 43.25 g of losartan potassium.

EXAMPLE 8

(Formation of Magnesium Salt of Losartan)

To 40.81 g of losartan of Example 1 in 235 ml of i-propanol, 6.07 g magnesium ethoxide were added, and stirred at reflux temperature overnight. Reaction mixture was hot filtered, 650 ml n-heptane were added, and cooled to room temperature for the product to precipitate. It was filtered and washed with 110 ml n-heptane, and dried in vacuo at 50° C. to yield 37.9 g losartan magnesium.

Melting point: above 300° C.

Assay of magnesium 2.9% (3.2% calculated to the anhydrous substance).

EXAMPLE 9

(Formation of Calcium Salt of Losartan)

To 40.81 g losartan of Example 1 in 235 ml i-propanol, 3.92 g calcium hydroxide were added, and it was stirred at reflux temperature for 1 hour, and hot filtered. 410 ml n-heptane were added to the filtrate and cooled to room temperature. The solvent was decanted from a resinous residue, and 820 ml n-heptane were added. It was stirred until a white solid crystallized. It was filtered, washed with 110 ml n-heptane, and dried in vacuo at 50° C. to yield 39.2 g losartan calcium.

Melting point: above 300° C.

Assay of calcium 4.0% (4.7% calculated to the anhydrous substance).

EXAMPLE 10

(Losartan Purified—Method 1)

35 g sodium salt of losartan were dissolved in 350 ml water, 106 ml of ethyl acetate were added, and it was acidified at a temperature of 21 to 25° C. to a pH of 3.6-3.8 with concentrated sulphuric acid, cooled below 10° C. and stirred for 1 hour. The formed solid was filtered, redispersed in 120 ml of ethyl acetate, filtered once again and dried in vacuo at 50° C. overnight to yield 29.3 g of losartan.

EXAMPLE 11

(Losartan Purified—Method 2)

42.66 g of potassium salt of losartan were dissolved in 430 ml water, 130 ml ethyl acetate were added, and it was acidified at a temperature of 21 to 25° C. to a pH of 3.6-3.8 with concentrated sulphuric acid, cooled below 10° C., and stirred for 1 hour. The formed solid was filtered, redispersed in 145 ml ethyl acetate, filtered once again, and dried in vacuo at 50° C. overnight to yield 36.6 g losartan.

EXAMPLE 12

(Losartan Purified—Method 3)

37.9 g magnesium salt of losartan were dissolved in 388 ml demineralized water, 120 ml of ethyl acetate were added, and it was acidified at a temperature of 21 to 25° C. to a pH of 3.6-3.8 with concentrated sulphuric acid, cooled below 10° C. and stirred for 1 hour. The formed solid was filtered, redispersed in 130 ml ethyl acetate, filtered once again, and dried in vacuo at 50° C. overnight to yield 32.3 g losartan.

EXAMPLE 13

(Losartan Purified—Method 4)

38.0 g calcium salt of losartan were dissolved in 380 ml water, 115 ml ethyl acetate were added, and it was acidified at a temperature of 21 to 25° C. to a pH of 3.6-3.8 with concentrated sulphuric acid, cooled below 10° C., and stirred for 1 hour. The formed solid was filtered, redispersed in 130 ml ethyl acetate, filtered once again, and dried in vacuo at 50° C. overnight to yield 36.2 g of losartan.

EXAMPLE 14

(Preparation of Pharmaceutically Usable Losartan Potassium Via Crystalline Losartan Sodium)

To 20.4 g crude losartan (chromatographic purity of 98.73%) in 120 ml i-propanol, a solution of 2.75 g sodium hydroxide in 2.9 ml water was added at a temperature of 38-40° C. to a pH of 10 during half an hour. Approximately 18 ml of azeotropic mixture i-propanol/water were removed by distillation, 70 ml n-heptane were added, and it was stirred at room temperature until a white solid was formed. The resulting solid was diluted with 28 ml n-heptane, filtered, washed with 55 ml n-heptane, and dried in vacuo at 50° C. to yield 18.5 g crystalline losartan sodium (yield: 87%, chromatographic purity: 99.42%).

The obtained substance was dissolved in 185 ml water, 56 ml ethyl acetate were added, and it was acidified at a temperature of 21-25° C. to a pH of 3.6-3.8 with concentrated sulphuric acid, cooled below 10° C., and stirred for 1 hour. The formed solid was filtered, redispersed in 64 ml ethyl acetate, filtered once again, and dried in vacuo at a temperature of 50° C. overnight to yield 16.5 g losartan (yield of the phase: 94%, chromatographic purity: 99.74%).

The resulting product was dissolved in 45 ml i-propanol, 4.39 g potassium tert-butoxide between 10° C. and 25° C. were added. The reaction mixture clarified. A dense, white precipitate was formed when 60 ml n-heptane were added, and it was stirred at room temperature for 1 hour. It was filtered and washed with 30 ml n-heptane, dried in vacuo at 50° C. overnight to yield 16.9 g losartan potassium (yield of the phase: 94%, chromatographic purity: 99.91%, overall yield: 77%).

EXAMPLE 15

(Preparation of Pharmaceutically Usable Losartan Potassium Via Crystalline Losartan Potassium)

As already described, to 10.2 g crude losartan of Example 14 (chromatographic purity 98.73%) in 59 ml i-propanol, a solution of 1.4 g potassium hydroxide in 1.5 ml water at a temperature of 38-40° C. to a pH of 10 over half an hour was added. Approximately 19 ml of azeotropic mixture i-propanol/water were removed by distillation, 36 ml n-heptane were added, and reaction mixture was stirred at room temperature until a white solid was formed. The resulting mixture was diluted with 14 ml n-heptane, filtered, washed with 26 ml n-heptane, and dried in vacuo at 50° C. to yield 8.57 g losartan potassium (yield: 77%, chromatographic purity: 99.67%).

The resulting potassium salt of losartan was dissolved in 86 ml water, 26 ml ethyl acetate were added, and it was acidified at a temperature of 21-25° C. to a pH of 3.6-3.8 with concentrated sulphuric acids, cooled below 10° C., and stirred for 1 hour. The formed solid was filtered, redispersed in 29 ml ethyl acetate, filtered once again, and dried in vacuo at 50° C. overnight to yield 7.35 g losartan (yield of the phase: 93%, chromatographic purity: 99.82%).

The resulting product was dissolved in 20 ml i-propanol, 1.96 g potassium t-butoxide in a temperature range between 10° C. and 25° C. were added. The reaction mixture clarified. Adense, white solid was formed when 27 ml n-heptane were added. Reaction mixture was stirred at room temperature for 1 hour, filtered and washed with 13 ml n-heptane, dried in vacuo at 50° C. overnight to yield 7.66 g losartan potassium (yield of the phase: 96%, chromatographic purity: 99.88%, total yield: 69%).

COMPARATIVE EXAMPLE 16

(Preparation of Potassium Salt According to Known Prior Art)

To 40.81 g losartan (chromatographic purity 98.73%) in 153 ml i-propanol, a mixture of 10 g potassium hydroxide, 5.1 ml water, and 100 ml i-propanol was added at a temperature of 38-40° C. to a pH of 10-11 during half an hour. Approximately 140 ml of the solvent (i-propanol/water mixture) were removed by distillation, and 92 ml n-heptane were added. It was stirred at room temperature until a white precipitate was formed. The precipitate was diluted with 54 ml n-heptane, filtered, washed with 70 ml n-heptane, and dried in vacuo at 50° C. to yield 38.4 g losartan potassium (yield: 86%, chromatographic purity: 99.67%).

EXAMPLE 17

(Amorphous Potassium Salt of Losartan—Method 1)

29.3 g purified losartan were suspended in 293 ml water. At room temperature the pH was adjusted to 9.3 with a 10% aqueous potassium hydroxide solution. The reaction mixture was clarified. The solution was filtered and lyophilized to yield 31.8 g white, completely amorphous product losartan potassium.

EXAMPLE 18

(Amorphous Potassium Salt of Losartan—Method 2)

20.0 g crystalline salt of losartan were dissolved in 200 ml distilled water. The clear solution was filtered and lyophilized to yield 20.0 g amorphous potassium salt of losartan.

EXAMPLE 19

(Preparation of Amorphous Losartan Potassium Salt by Evaporation)

1.0 g losartan potassium salt (Form I) was dissolved in 20 ml methanol or ethanol. The clear solution was filtered and evaporated in vacuo to a dry residue at 50° C. Yield of 1.12 g.

EXAMPLE 20

(Preparation of Amorphous Losartan Potassium Salt by Evaporation)

1 g losartan potassium salt (Form I) was dissolved in 100 ml i-propanol or 30 ml n-propanol. The clear solution was filtered and evaporated in vacuo to a dry residue at 50° C. Yield of 1.1 g.

EXAMPLE 21

(Amorphous Sodium Salt of Losartan—Method 1)

5.0 g purified losartan were suspended in 50 ml water. At room temperature the pH was adjusted to 9.62 with a 10% aqueous sodium hydroxide solution. The reaction mixture clarified. The solution was filtered and lyophilised to yield 5.2 g amorphous sodium salt of losartan.

EXAMPLE 22

(Amorphous Sodium Salt of Losartan—Method 2)

3.10 g of crystalline losartan sodium were dissolved in 31 ml water. The clear solution was filtered and lyophilised to yield 3.10 g amorphous sodium salt of losartan.

Melting point: 171-177° C.

EXAMPLE 23

(Formation of Losartan Potassium from Losartan Potassium Form I in Wet Diethylether)

10.0 g losartan potassium salt (Form I) were suspended in 500 ml diethylether. During intnesive stirring, 5 ml water were added to the suspension at room temperature, whereat water was partially dissolved in ether. It was stirred overnight and the formed precipitate filtered, and dried in vacuo at 45° C. for 2 hours. Yield of 9.5 g.

EXAMPLE 24

(Formation of Crystalline Form with Bound Water from Losartan Potassium of Form I in Wet Ethyl Acetate)

10.0 g losartan potassium salt (Form I) were suspended in 500 ml ethyl acetate. During intensive stirring 5 ml of water was added to the suspension at room temperature, It was stirred overnight and the formed crystalline solid filtered and dried in vacuo at 45° C. for 3 hours. Yield 9.3 g.

EXAMPLE 25

(Formation of Crystalline Form with Bound Water with the Traces of Form I Losartan Potassium Salt)

10 g losartan potassium salt (Form I) were suspended in 500 ml diisopropylether. During intensive stirring, 1.2 ml water were added to the suspension at room temperature. It was stirred overnight and the formed crystalline solid filtered, and dried in vacuo at 45° C. for 3 hours. Yield 9.6 g.

EXAMPLE 26

(Conversion of Losartan Potassium Form I in Wet Heptane)

10 g losartan potassium salt (Form I) were suspended in 100 ml n-heptane. During intensive stirring, 1.2 ml water were added to the suspension at room temperature. It was stirred overnight. The formed precipitate was filtered, and dried in vacuo at 45° C. for 3 hours. Yield 10 g. Crystalline form with bound water was essentially formed. The product might contain other polymorphic forms in traces.

EXAMPLE 27

(Formation of Crystalline Form with Bound Water from Losartan Potassium Form I in Water)

5.0 g of losartan potassium salt (Form I) was dissolved in 2.5 ml of water in a 10-ml reaction flask at room temperature, and after about 5 minutes the product crystallized. The flask with the contents was dried in vacuo at 50° C. for 6 hours, the contents were transferred to the mortar, ground and dried again in vacuo for 3 hours. Yield 4.3 g of the product.

EXAMPLE 28

Formation of Crystalline Form with Bound Water in Water and by Redispersing in Diethylether)

1.0 g losartan potassium salt was dissolved in 0.5 ml water at room temperature. After about 5 minutes the product crystallized, 50 ml of diethylether (or DIPE) were added, and it was intensively stirred for 1 hour. The resulting solid was filtered, and dried in vacuo at 45° C. 2 hours. Yield of 1.0 g.

EXAMPLE 29

(Formation of Crystalline Form with Bound Water from Losartan Potassium Form I in Water and by Redispersing in Diisopropylether)

1.0 g of losartan potassium salt (Form I) was dissolved in 0.5 ml of water at room temperature. After about 5 minutes the product crystallized, 50 ml of diisopropylether was added and intensively stirred for 1 hour to suspend. The resulting precipitate was filtered and dried in vacuo at 45° C. for 3 hours. Yield 1.0 g.

EXAMPLE 30

(Formation of Crystalline Form with Bound Water from Losartan Potassium Form I in Water and by Redispersing in Heptane)

1 g losartan potassium salt (Form I) was dissolved in 0.5 ml of water at room temperature. After about 15 minutes the product crystallized, and while stirring intensively, 10 ml n-heptane were added, and it was stirred overnight. The resulting solid was filtered, and dried. Yield 1 g.

EXAMPLE 31

(Formation of Crystalline Form with Bound Water from Amorphous Losartan Potassium in Wet Heptane)

1 g amorphous losartan potassium salt was suspended in 10 ml n-heptane. While stirring intensively, 0.12 ml water were added to the suspension at room temperature. It was stirred overnight; the resulting solid was filtered, and dried. Yield 0.85 g.

EXAMPLE 32

(Formation of Crystalline Form with Bound Water from Amorphous Losartan Potassium in Wet Diethylether)

1 g amorphous losartan potassium salt was dissolved in 0.5 ml water at room temperature. After about 15 minutes the product crystallized, 50 ml diethylether were added, and it was intensively stirred overnight. The resulting solid was filtered, and dried. Yield 0.9 g.

EXAMPLE 33

(Formation of Crystalline Form with Bound Water from Amorphous Losartan Potassium in Wet Ethyl Acetate)

1.0 g amorphous losartan potassium salt was suspended in 10 ml ethyl acetate. While intensively stirring, 0.12 ml water wee added to the suspension at room temperature. It was stirred overnight, and the resulting solid was filtered, and dried in vacuo at 45° C. for 3 hours. Yield of 0.87 g.

EXAMPLE 34

(Formation of Crystalline Form with Bound Water from Amorphous Losartan Potassium in Water and by Redispersing in Diethylether)

1.0 g of amorphous losartan potassium salt was dissolved in 0.5 ml water at room temperature. After about 15 minutes the product crystallized, 50 ml diethyl ether were added, and it was stirred intensively overnight. The resulting solid was filtered, and dried in vacuo at 45° C. for 3 hours. Yield 0.9 g.

EXAMPLE 35

(Formation of Crystalline Form with Bound Water from Amorphous Losartan Potassium in Humid Atmosphere)

Amophous losartan potassium (about 0.5 g) was uniformly distributed on the bottom of a Petri dish, which was uncovered placed in a desiccator with controlled relative humidity (80%, KBr solution). The sample dissolved after about 45-60 minutes (a transparent viscous mass was formed), and then crystallized (white crystals were produced).

EXAMPLE 36

(Thermogravimetric Analysis)

The content of water in crystalline form with bound water of losartan potassium was determined by thermogravimetric analysis. According to calculation, trihydrate substance would contain 10.5% water, and would exhibit a 3.5% change in the weight due to each molecule of water per molecule of losartan.

TG measurements clearly indicated that water loss occurred in two steps. The limit between the steps was between 50° C. and 60° C. wherein in the first step the sample lost about 3 to 4% of the weight, in the second step the loss was about 7 to 8%, totally about 12%.

EXAMPLE 37

(DVS Measurements)

During the DVS experiment, in the starting amorphous sample the weight increased by 20-26% at 70-80% relative humidity. At higher increase of relative humidity, the weight of the sample decreased to about below 13% water, which indicated crystallization. From the amorphous state a crystal structure crystallized whereat surplus water separated from an orderly-state structure which could be visualized as a sudden drop of weight. In the repetitive circle of sorption/descorption of water, the moisture in the sample did not increase above the equilibrium moisture in the crystal (it absorbed less water than previously the amorphous form). DVS measurements also confirmed that water was crystally bound as hydrate, as they clearly showed that during drying of the crystal substance, there was no loss of moisture, however the water was lost relatively quickly at the end when the relative humidity dropped below 20%.

During heating under reduced pressure (at about 0.3 mbar) crystal-bound water was lost and the formed substance was amorphous again.

EXAMPLE 38

(DSC Analysis of Amorphous Losartan Potassium Salt)

DSC diagram of amorphous losartan potassium salt was recorded. To 110° C. a stretched endothermic peak was visible denoting loss of water. At 128-129° C. there was a saddle denoting a glassy conversion of the amorphous substance. At 201-220° C. there was a well-marked peak resulting from an orderly-state structure into the crystal lattice (crystallization). On the DSC curve later on, no conversion to the other polymorphic form was visible as it was visible during heating of crystalline polymorphic Form I which converted to Form II at 240° C. Crystals of the substance began to melt at 273° C., melting was followed by decomposition, being the same as in the crystalline substance.

EXAMPLE 39

(DSC Analysis of Crystalline Form with Bound Water of Losartan Potassium)

DSC diagram of the crystalline form with bound water of losartan potassium salt was recorded.

To 75° C. a stretched peak was visible; denoting loss of first water, about 90° C. a sharp endothermic peak denoting simultaneous loss of the other two waters and destruction of the ordered state to amorphous (an amorphous form of the substance has a higher level of disordered state and thus higher entropy than crystalline form, thus the conversion of a crystal to an amorphous Form Is an endothermic process). At 190-200° C. the amorphous substance crystallized again.

EXAMPLE 40

(Stability)

Amorphous losartan potassium was essentially more hygroscopic than the form with bound water of losartan potassium. For evaluation and comparison, respectively, of the stability, four tests were conducted. The amorphous substance was compared with the form with bound water, both exposed for 4 days in the atmosphere of air under the conditions:

Example 40a: 60° C., dry atmosphere
Example 40b: 60° C., moisture
Example 40c: 80° C., dry atmosphere
Example 40d: 80° C. moisture The results indicated that the crystalline form with bound water was at least as stable as amorphous (to temperature and moisture). Exposed to moisture amorphous losartan potassium merged into a glassy mass and then white crystals of form with bound water were formed; in the parallel test the crystalline form with bound water of losartan potassium maintained the powdered form when exposed to moisture. Both forms of substances were very similar by the assays of degradation products.

EXAMPLE 41

(Dependence of XRD on Temperature)

An X-ray diffraction spectra of a sample of the crystalline form with bound water of losartan potassium was measured at temperatures: 25, 40, 60, 90, 120 and 240° C. Heating to individual temperature was at the rate of 10° C./min. Measurement at one temperature lasted for 59 minutes. Total time of the measurement was 7 hours and 22 minutes. This time also takes into account the heating time. The amorphous substance was formed from crystalline form with bound water above about 60° C. that crystallized at higher temperature again.

EXAMPLE 42

10 g of potassium salt of losartan Form I were dissolved in a mixture of 200 ml methanol and 1.2 ml water. The resulting solution was concentrated to a volume of 13 ml and, while stirring at room temperature, it was poured to 500 ml diethyl ether. The resulting solid was stirred at room temperature for 1 hour, filtered, and dried in vacuo at 45° C. Yield 9.3 g.

EXAMPLE 43

(Preparation of Potassium Salt of Losartan Containing Polymorph Form X)

10 g potassium salt of losartan Form I were dissolved in a mixture of 200 ml methanol and 1.2 ml water. The resulting solution was concentrated to a volume of 35 ml and, while stirring at room temperature, it was poured to 500 ml diisopropyl ether. The resulting solid was stirred at room temperature for 1 hour, filtered, and dried. Yield 9.93 g.

EXAMPLE 44a (Preparation of Polymorph Form X of Potassium Salt of Losartan)

1 g potassium salt of losartan Form I was dissolved in 20 ml methanol. The resulting solution was concentrated to a dense glassy mass and, while stirring at room temperature, it was poured to 100 ml n-hexane. The resulting solid was stirred at room temperature for 1 hour, and filtered. It was carefully dried. Yield 0.92 g.

EXAMPLE 44b (Preparation of Polymorph Form X of Potassium Salt of Losartan)

1 g potassium salt of 2-n-butyl-4-chloro-5-hydroxymethyl-1-[[2'-(1H-tetrazol-5-yl)[1,1'-biphenyl]-4-yl]methyl]-1H-imidazole Form I was dissolved in 20 ml methanol. The resulting solution was concentrated to a dense glassy mass and, while stirring at room temperature, it was poured into 100 ml n-heptane. The resulting solid was stirred at room temperature for 1 hour, filtered, and dried. Yield 0.92 g. The batch was coded as LST-K-3279. Analogously, batch LST-K-1481 was prepared, which was additionally ground on a mill Alpine MFC at 5000 rpm and a 0.5 mm screen, and the milled batch was coded as LST-K-1496/1.

The sample coded as LST-K-3279 did not change its polymorphic forms after a 45-day storage in a closed flask at room temperature. The sample was exposed to temperatures between 60° C. and 80° C. and negative pressure ~10 mBar. The crystalline structure did not change under any of the conditions. Exposed to the above conditions, the sample lost 0.79% (60° C.) and 0.90% (80° C.) of its weight.

EXAMPLE 45

(Preparation of Polymorph Form Y of Potassium Salt of Losartan)

10 g potassium salt of 2-n-butyl-4-chloro-5-hydroxymethyl-1-[[2'-(1H-tetrazol-5-yl)[1,1'-biphenyl]-4-yl]methyl]-1H-imidazole were dissolved in 200 ml of industrial grade methanol. The clear solution was evaporated to a dense but still clear residue just before it began crystallizing (to a weight of about 13 g), to which 1000 ml n-hexane were added while stirring at room temperature. It was stirred at room temperature for further 2 hours and filtered. Yield 9.7 g

EXAMPLE 46

(Alternative Mode of Preparing Polymorph Form Y of Potassium Salt of Losartan)

10 g potassium salt of 2-n-butyl-4-chloro-5-hydroxymethyl-1-[[2'-(1H-tetrazol-5-yl)[1,1'-biphenyl]-4-yl]methyl]-1H-imidazole were dissolved in 12.5 ml methanol. While stirring, to the clear solution into 500 ml of n-hexane, that had previously been seeded with several crystals of a potassium salt of polymorph Form Y, were added. It was carefully stirred at room temperature, and filtered. Yield of 7.9 g. The batch with the code L-3391/A was prepared in a similar manner as described in the above Examples.

Temperature stability of the sample of polymorph Form Y was tested by exposing 10 g polymorph Form Y potassium salt of -n-butyl-4-chloro-5-hydroxymethyl-1-[[2'-(1H-tetrazol-5-yl)[1,1'-biphenyl]-4-yl]methyl]-1H-imidazole to heat while dried. Polymorph Form X was obtained. Yield 9.1 g

EXAMPLE 47

20 g purified 2-n-butyl-4-chloro-5-hydroxymethyl-1-[[2'-(1H-tetrazol-5-yl)[1,1'-biphenyl]-4-yl]methyl]-1H-imidazole were suspended in 200 ml water. At room temperature the pH was adjusted to 9.3 with a 10% aqueous potassium hydroxide solution. The reaction mixture was clarified. The solution was filtered, and lyophylized to yield 19.74 g of a white, completely amorphous product. The test was repeated with different amounts of water so that additional 20% and 30% solutions were lyophilized, and batches LST-K-1434/1 (10% solution), LST-K-1434/2 (20% solution) and LST-K-1434/3 (30% solution) were obtained.

EXAMPLE 48

(Determination of the Particle Size and Specific Surface Area)

The particle size was determined by the method of scattering the laser light (Malvern). The results clearly indicated that the smallest particles were in the sample LST-K-1434/1, the largest being in LST-K-1434/3. The specific surface area is indirectly proportional to the particle size: the largest in the sample of batch LST-K-1434/1, and the smallest in the sample of batch LST-K-1434/3. In addition to the particle size, for the samples LST-K-1481 and LST-K-1496/2, the solubility parameters were determined. Results are given in Tables 4 and 5.

EXAMPLE 49

(Determination of Bulk and Tapped Density and Flow Poperties)

Table 3 presents bulk and tapped volumes/densities of the samples prepared according to Example 47, Batch LST-K-1434/3, also having the largest particles, is the most suitable for pharmaceutical use, results being presented in Table 6.

EXAMPLE 50

(Solid Pharmaceutical Composition Containing a Potassium Salt of Losartan)

Film coated tablets were prepared with core contents, as follows:

| | |
|---|---|
| losartan potassium | 50.00 mg |
| lactose monohydrate | 28.52 mg |
| microcrystalline cellulose | 60.00 mg |
| pregelatinized starch | 20.00 mg |
| aerosil | 0.48 mg |
| magnesium stearate | 1.00 mg |

For film coating the following was used:

| | |
|---|---|
| hydroxypropylmethylcellulose | 1.984 mg |
| hydroxypropylcellulose | 0.496 mg |
| polyethylene glycol | 0.400 mg |
| titanium dioxide | 0.920 mg |

Tablets were prepared by direct dry blend procedure. A blend of the active substance with lactose, microcrystalline cellulose, starch and aerosol was prepared, and the mixture was sieved. Magnesium stearate was added, and the entirety was rehomogenized. Cores weighing 160 mg were compressed into tablets. The film coating prepared from the listed ingredients as a suspension in demineralized water was applied on the cores. The coated tablets were polished with talc.

EXAMPLE 51

(Solid Pharmaceutical Composition Containing Losartan Potassium and Hydrochlorothiazide)

Tablets containing in the core:

| | |
|---|---|
| losartan potassium | 50.00 mg |
| hydrochlorothiazide | 12.50 mg |
| lactose monohydrate | 26.90 mg |
| microcrystalline cellulose | 60.00 mg |
| pregelatinized starch | 23.60 mg |
| aerosil | 0.50 mg |
| magnesium stearate | 1.50 mg | and the coating:

| | |
|---|---|
| hydroxypropylmethylcellulose | 1.925 mg |
| hydroxypropylcellulose | 1.925 mg |
| titanium dioxide | 1.130 mg |
| iron oxide E 172 | 0.020 mg | were prepared by the dry granulation method by slugging. The active substances losartan potassium and hydrochlorothiazide were mixed with starch and aerosol first and the mixture was sieved. Lactose, microcrystalline cellulose and the remaining quantity of aerosol were added, sieved, and the mixture was slugged. The slugs were ground, magnesium stearate was added and the granulatation homogenized. The cores weighing 175 mg were compressed into tablets. The film coating prepared from the listed ingredients as the suspension in demineralized water was applied on the cores. The film-coated tablets were polished with talc.

EXAMPLE 52a (Film Coated Tablets)

Composition of a tablet

| | |
|---|---|
| core | |
| Losartan potassium | 100.000 mg |
| Silicified Mycrocrystalline Cellulose | 199.200 mg |
| Croscarmellose Sodium | 16.000 mg |
| Silica Colloidalis Anhydrica | 3.200 mg |
| Magnesium stearate | 1.600 mg |
| coating | |
| Hydroxypropylcellulose | 4360 mg |
| Ethylcellulose | 6.540 mg |
| Triethyl citrate | 2.000 mg |
| Titanium dioxide | 1.080 mg |
| Ferric oxide red | 0.020 mg |
| Talc | 2.000 mg |
| Weight | 336.000 mg |
| *Ethanol | 120.000 mg |
| "Talc | 0.220 mg |

*Ethanol is removed during the process
"Talc is not included into the coating polishing agent Preparation Procedure:

Losartan potassium and silica coloidalis anhydrica were mixed, then silicified mycrocrystalline cellulose and croscarmelose sodium were added, and homogenized by mixing for 10 minutes. The dry mixture was sieved before magnesium stearate was added, and the final mixture was blended for 3 min. The final dry mixture was compressed on a rotary tabletting machine.

The tablet cores produced had a weight of 320 mg, a diameter of 10 mm, and possessed satisfactory technical properties.

Hydroxypropylcellulose, (Klucel EF), ethylcellulose (N7) and triethyl citrate were dissolved by stirring in ethanol, and then homogenized (Ultraturax. 30 min.). A suspension of titanium dioxide, ferric oxide red, and talc in ethanol was added. Prepared dispersion was sprayed onto cores so that a film coating in a weight ratio of about 4.8 wt. % with regard to the core was obtained. Tablets were polished with talc.

EXAMPLE 52b (Film Coated Tablets)

Composition of a Tablet

| core | |
|---|---|
| Losartan potassium | 100.000 mg |
| Silicified Mycrocrystalline Cellulose | 199.200 mg |
| Croscarmellose Sodium | 16.000 mg |
| Silica Colloidalis Anhdrica | 3.200 mg |
| Magnesium stearate | 1.600 mg |
| coating | |
| Hydroxypropylcellulose | 10.900 mg |
| Stearic acid | 2.100 mg |
| Triethyl citrate | 0.800 mg |
| Titanium dioxide | 1.080 mg |
| Ferric oxide red | 0.020 mg |
| Talc | 1.100 mg |
| Weight | 336.000 mg |
| *Ethanol | 140.000 mg |
| "Talc | 0.220 mg |

*Ethanol is removed during the process
"Talc is not included into coating, polishing agent Preparation Procedure:

Losartan potassium and silica coloidalis anhydrica were mixed, then silicified mycrocrystalline cellulose, and croscarmelose sodium were added, and homogenized by mixing for 10 minutes. The dry mixture was sieved before adding magnesium stearate, and the final mixture was blended for 3 min. The final dry mixture was compressed on a rotary tabletting machine. The tablets produced had a weight of 320 mg. a diameter of 10 mm, and possessed satisfactory technical properties.

Hydroxypropylcellulose, (Klucel EF), and Triethyl citrate (4.800 g) were dissolved with stirring in ethanol, and then homogenized (Ultraturax. 30 min.). Suspension of titanium dioxide, ferric oxide red, talc and stearic acid in ethanol was added.

Prepared dispersion was sprayed onto cores so the film coating in a weight ratio of about 4.8 wt. % regard to the core was obtained. Tablets were also polished with talc.

EXAMPLE 53

(Dissolution of Film Coated Tablets)

Tablets prepared were subjected to a dissolution test.

| Minutes | Example 53a $\overline{X}$ % | Example 53b $\overline{X}$ % |
|---|---|---|
| 10 | 18.0 | 67.7 |
| 20 | 80.2 | 86.0 |
| 30 | 92.5 | 88.8 |
| 45 | 95.5 | 93.0 |
| 60 | 98.1 | 94.4 |

EXAMPLE 54

(Industrial Scale Preparation of Crystalline Losartan Potassium)

Into a reactor, 45.7 l of THF and 9.6 kg of 2-n-butyl-4-chloro-5-hydroxymethy-1-[2'-triphenylmethyl-2H-tetrazol-5-yl) [1,1'-biphenyl-4-yl]methyl]imidazole were loaded. Separately prepared, a solution of 15.3 kg 12% HCl was added to the reaction mixture, further a 30% solution of NaOH was added into reaction mixture until the pH reached around 12. The solvent was removed by distillation, water was added, and the reaction mixture was extracted with toluene. To the water phase ethyl acetate was added and, further, diluted sulphuric acid was added until the pH, was around 4, by cooling. The crystals formed were filtered.

5.9 kg of amphoter product of the previous stage were added to 16 l of i-propanol, 1.57 kg potassium t-butylate was added, after two hours of mixing or reaction mixture some heptane was added, and thick precipitate was formed, which was washed by heptane.

Up to 7 kg crude wet product of previous stage was added to 100 to 150 l isopropanol, heated, purified with activated carbon, filtered and concentrated to approximately one fourth of the volume, 12 to 16 kg n-heptane were added, and the reaction mixture was slowly cooled under continuous intensive stirring. Thus formed crystals were dried, and milled.

EXAMPLE 55

(Industrial Scale Preparation of Crystalline Losartan Potassium for Incorporation into a Pharmaceutical Composition)

A solution of 500 g losartan potassium in methanol was filtered and concentrated in vacuo to a volume of 650 ml. (Optionally in a parallel experiment n-heptane was added to the concentrated solution). The solution was seeded with source crystals of Form X and stirred intensively at room temperature for 3 hours. The white suspension was evaporated to dryness, and dried at 80° C. to give 496.9 g of product.

EXAMPLE 56

(Industrial Scale Preparation of Crystalline Losartan Potassium)

A solution of 4.2 kg losartan potassium in 10 kg methanol was filtered and concentrated in vacuum to a volume of 6.3 l.

The solution was seeded with source crystals of Form X and stirred at room temperature for 2 hours. The white suspension was evaporated to dryness and dried at 65° C. (optionally to 80° C.) in vacuum to give 3.8 kg of product.

The invention claimed is:

1. A potassium salt of losartan in crystal Form X characterized by a powder X-ray diffraction pattern essentially as depicted in FIG. 31 and having a melting point of about 230° C. to about 237° C.

2. A potassium salt of losartan in crystal Form X according to claim 1 which is characterized by a purity of at least about 99% by weight.

3. A potassium salt of losartan in crystal Form X according to claim 1 which is characterized by a purity of at least about 99.80% by weight.

4. Characterized by a powder X-ray diffraction pattern essentially as depicted in FIG. 31, with peaks at about 6.9, 13.8, 19.1, 20.6, 21.4, 24.0, 24.8, 25.9, 28.7 and 29.2±0.2 degrees 2 ⊖; and having a melting point of about 230° C. to about 237 ° C., wherein said potassium salt of losartan is in the form of particles and wherein at least about 50% of said particles have a diameter of about 5 μm to about 500 μm.

5. A potassium salt of losartan in crystal Form X according to claim 1 wherein at least about 50% of particles have a diameter less than about 100 μm.

* * * * *